United States Patent
Sack

(10) Patent No.: US 11,246,716 B2
(45) Date of Patent: Feb. 15, 2022

(54) IMPLANT WITH DEPLOYABLE BLADES

(71) Applicant: Institute for Musculoskeletal Science and Education, Ltd., King of Prussia, PA (US)

(72) Inventor: James A. Sack, Elverson, PA (US)

(73) Assignee: Institute for Musculoskeletal Science and Education, Ltd., King of Prussia, PA (US)

( * ) Notice: Subject to any disclaimer, the term of this patent is extended or adjusted under 35 U.S.C. 154(b) by 281 days.

(21) Appl. No.: 16/429,278

(22) Filed: Jun. 3, 2019

(65) Prior Publication Data
US 2019/0282372 A1 Sep. 19, 2019

Related U.S. Application Data

(63) Continuation of application No. 15/296,902, filed on Oct. 18, 2016, now Pat. No. 10,307,265.

(51) Int. Cl.
*A61F 2/44* (2006.01)
*A61F 2/30* (2006.01)

(52) U.S. Cl.
CPC ............ *A61F 2/447* (2013.01); *A61F 2/4455* (2013.01); *A61F 2002/3039* (2013.01);
(Continued)

(58) Field of Classification Search
CPC .................... A61F 2/447; A61F 2/4455; A61F 2002/30387; A61F 2002/3039;
(Continued)

(56) References Cited

U.S. PATENT DOCUMENTS 5,609,635 A 3/1997 Michelson
5,683,394 A 11/1997 Rinner
(Continued)

FOREIGN PATENT DOCUMENTS

CN 2730337 10/2005
CN 101854887 10/2010
(Continued)

OTHER PUBLICATIONS

Office Action dated Apr. 9, 2020 in U.S. Appl. No. 16/109,326.
(Continued)

*Primary Examiner* — Jessica Weiss
(74) *Attorney, Agent, or Firm* — Plumsea Law Group, LLC

(57) ABSTRACT

An implant, comprising a body having a superior surface and an inferior surface, a superior-inferior axis, and a lateral axis. The implant further includes a first blade having a first retracted position in the body and a first extended position where the first blade extends outwardly from the body. In addition, the implant may include a blade actuating member that can translate through the body in directions parallel to the lateral axis. When the blade actuating member is moved in a first direction along the first axis, the first blade moves towards the first extended position. When the blade actuating member is moved in a second direction opposite the first direction, the first blade moves towards the first retracted position. Further, in the first extended position, the first blade extends from the superior surface at a first non-zero angle with respect to the superior-inferior axis.

20 Claims, 20 Drawing Sheets

(52) U.S. Cl.
CPC ............... *A61F 2002/3093* (2013.01); *A61F 2002/30387* (2013.01); *A61F 2002/30433* (2013.01); *A61F 2002/30507* (2013.01); *A61F 2002/30515* (2013.01); *A61F 2002/30518* (2013.01); *A61F 2002/30578* (2013.01); *A61F 2002/30579* (2013.01); *A61F 2002/30593* (2013.01); *A61F 2002/30622* (2013.01); *A61F 2002/30677* (2013.01); *A61F 2002/30841* (2013.01)

(58) Field of Classification Search
CPC .. A61F 2002/30433; A61F 2002/30507; A61F 2002/30515; A61F 2002/30518; A61F 2002/30578; A61F 2002/30579; A61F 2002/30593; A61F 2002/30622; A61F 2002/30677; A61F 2002/30841; A61F 2002/3093
USPC ............................................ 623/17.11–17.16
See application file for complete search history.

(56) References Cited

U.S. PATENT DOCUMENTS

| | | |
|---|---|---|
| 5,702,391 A | 12/1997 | Lin |
| 5,800,547 A | 9/1998 | Schafer et al. |
| 5,800,550 A | 9/1998 | Sertich |
| 6,102,950 A | 8/2000 | Vaccaro |
| 6,113,638 A | 9/2000 | Williams |
| 6,179,873 B1 | 1/2001 | Zientek |
| 6,251,140 B1 | 6/2001 | Marino |
| 6,447,546 B1 | 9/2002 | Bramlet |
| 6,478,823 B1 | 11/2002 | Michelson |
| 6,520,993 B2 | 2/2003 | James et al. |
| 6,527,803 B1 | 3/2003 | Crozet et al. |
| 6,726,720 B2 | 4/2004 | Ross et al. |
| 6,767,367 B1 | 7/2004 | Michelson |
| 6,800,092 B1 | 10/2004 | Williams |
| 7,214,243 B2 | 5/2007 | Taylor |
| 7,217,293 B2 | 5/2007 | Branch, Jr. |
| 7,223,289 B2 | 5/2007 | Trieu |
| 7,569,074 B2 | 8/2009 | Eisermann |
| 7,594,931 B2 | 9/2009 | Louis |
| 7,594,932 B2 | 9/2009 | Aferzon |
| 7,655,046 B2 | 2/2010 | Dryer |
| 7,749,274 B2 | 7/2010 | Razian |
| 7,771,475 B2 | 8/2010 | Michelson |
| 7,879,099 B2 | 2/2011 | Zipnick |
| 7,972,365 B2 | 7/2011 | Michelson |
| 7,981,157 B2 | 7/2011 | Castleman et al. |
| 7,998,211 B2 | 8/2011 | Baccelli et al. |
| 8,062,375 B2 | 11/2011 | Glerum |
| 8,070,812 B2 | 12/2011 | Keller |
| 8,070,819 B2 | 12/2011 | Aferzon |
| 8,075,618 B2 | 12/2011 | Trieu |
| 8,080,062 B2 | 12/2011 | Armstrong et al. |
| 8,100,972 B1 | 1/2012 | Bruffey et al. |
| 8,142,508 B1 | 3/2012 | Bruffey |
| 8,147,556 B2 | 4/2012 | Louis |
| 8,182,539 B2 | 5/2012 | Tyber et al. |
| 8,216,313 B2 | 7/2012 | Moore |
| 8,221,502 B2 | 7/2012 | Branch, Jr. |
| 8,257,439 B2 | 9/2012 | Zeegers |
| 8,267,997 B2 | 9/2012 | Colleran |
| 8,273,125 B2 | 9/2012 | Baccelli et al. |
| 8,292,958 B1 | 10/2012 | Bruffey |
| 8,328,870 B2 | 12/2012 | Patel |
| 8,343,219 B2 | 1/2013 | Allain |
| 8,366,774 B1 | 2/2013 | Bruffey |
| 8,377,138 B2 | 2/2013 | Reo |
| 8,409,285 B2 | 4/2013 | Keller |
| 8,460,388 B2 | 6/2013 | Kirwan |
| 8,491,658 B1 | 7/2013 | Etminan |
| 8,512,409 B1 | 8/2013 | Mertens et al. |
| 8,518,120 B2 | 8/2013 | Glerum |
| 8,523,946 B1 | 9/2013 | Swann |
| 8,556,979 B2 | 10/2013 | Glerum |
| 8,679,183 B2 | 3/2014 | Glerum |
| 8,685,098 B2 | 4/2014 | Glerum |
| 8,698,405 B2 | 4/2014 | Kirwan |
| 8,709,086 B2 | 4/2014 | Glerum |
| 8,864,833 B2 | 10/2014 | Glerum |
| 8,888,853 B2 | 11/2014 | Glerum |
| 8,888,854 B2 | 11/2014 | Glerum |
| 8,968,405 B2 | 3/2015 | Kirwan et al. |
| 9,039,771 B2 | 5/2015 | Glerum |
| 9,198,774 B2 | 12/2015 | Pisharodi |
| 9,463,091 B2 | 10/2016 | Brett |
| 9,566,163 B2 | 2/2017 | Suddaby et al. |
| 9,675,470 B2 | 6/2017 | Packer et al. |
| 9,707,100 B2 | 7/2017 | Duffield et al. |
| 9,730,802 B1 | 8/2017 | Harvey |
| 2003/0109928 A1 | 6/2003 | Pasquet |
| 2003/0149484 A1 | 8/2003 | Michelson |
| 2003/0187436 A1 | 10/2003 | Bolger et al. |
| 2004/0254644 A1 | 12/2004 | Taylor |
| 2005/0027362 A1 | 2/2005 | Williams et al. |
| 2005/0033429 A1 | 2/2005 | Kuo |
| 2005/0049590 A1 | 3/2005 | Alleyne et al. |
| 2005/0107788 A1 | 5/2005 | Beaurain |
| 2005/0125062 A1 | 6/2005 | Biedermann et al. |
| 2005/0197760 A1 | 9/2005 | Kaga |
| 2006/0069436 A1 | 3/2006 | Sutton et al. |
| 2006/0282074 A1 | 12/2006 | Renaud |
| 2007/0162130 A1 | 7/2007 | Rashbaum |
| 2007/0270961 A1 | 11/2007 | Ferguson |
| 2008/0021562 A1 | 1/2008 | Huppert |
| 2008/0051901 A1 | 2/2008 | deVilliers |
| 2008/0051902 A1 | 2/2008 | Dwyer |
| 2008/0133017 A1 | 6/2008 | Beyar et al. |
| 2008/0234686 A1 | 9/2008 | Beaurain |
| 2008/0312743 A1 | 12/2008 | Vila |
| 2009/0164020 A1 | 6/2009 | Janowski |
| 2009/0182430 A1 | 7/2009 | Tyber |
| 2009/0265007 A1 | 10/2009 | Colleran |
| 2009/0292316 A1 | 11/2009 | Hess |
| 2010/0010547 A1 | 1/2010 | Beaurain |
| 2010/0016974 A1 | 1/2010 | Janowski |
| 2010/0145459 A1 | 6/2010 | McDonough et al. |
| 2010/0185289 A1 | 7/2010 | Kirwan et al. |
| 2010/0185292 A1 | 7/2010 | Hochschuler et al. |
| 2010/0204737 A1 | 8/2010 | Bae |
| 2010/0249935 A1 | 9/2010 | Slivka |
| 2010/0280618 A1 | 11/2010 | Jodaitis |
| 2010/0305704 A1 | 12/2010 | Messerli |
| 2011/0015742 A1 | 1/2011 | Hong |
| 2011/0015745 A1 | 1/2011 | Bucci |
| 2011/0035007 A1 | 2/2011 | Patel |
| 2011/0077739 A1 | 3/2011 | Rashbaum |
| 2011/0093074 A1 | 4/2011 | Glerum et al. |
| 2011/0098747 A1 | 4/2011 | Donner |
| 2011/0118840 A1 | 5/2011 | Huntsman |
| 2011/0160866 A1 | 6/2011 | Laurence |
| 2011/0166655 A1 | 7/2011 | Michelson |
| 2011/0178599 A1 | 7/2011 | Brett |
| 2011/0208311 A1 | 8/2011 | Janowski |
| 2011/0230970 A1 | 9/2011 | Lynn et al. |
| 2011/0230971 A1 | 9/2011 | Donner et al. |
| 2011/0313528 A1 | 12/2011 | Laubert |
| 2012/0035729 A1 | 2/2012 | Glerum |
| 2012/0053693 A1 | 3/2012 | Zeegers |
| 2012/0078301 A1 | 3/2012 | Hess |
| 2012/0078371 A1 | 3/2012 | Gamache |
| 2012/0078373 A1 | 3/2012 | Gamache et al. |
| 2012/0095559 A1 | 4/2012 | Woods et al. |
| 2012/0116466 A1 | 5/2012 | Dinville |
| 2012/0150300 A1 | 6/2012 | Nihalani |
| 2012/0150304 A1 | 6/2012 | Glerum |
| 2012/0150305 A1 | 6/2012 | Glerum |
| 2012/0158146 A1 | 6/2012 | Glerum |
| 2012/0158148 A1 | 6/2012 | Glerum |
| 2012/0185049 A1 | 7/2012 | Varela |
| 2012/0191196 A1 | 7/2012 | Louis |
| 2012/0215315 A1 | 8/2012 | Hochschuler et al. |

(56) References Cited

U.S. PATENT DOCUMENTS

| | | |
|---|---|---|
| 2012/0265248 A1 | 10/2012 | Delecrin |
| 2012/0277867 A1 | 11/2012 | Kana et al. |
| 2012/0330417 A1 | 12/2012 | Zipnick |
| 2012/0330424 A1 | 12/2012 | Zeegers |
| 2013/0013006 A1 | 1/2013 | Rashbaum |
| 2013/0041408 A1 | 2/2013 | Dinville |
| 2013/0053891 A1 | 2/2013 | Hawkins |
| 2013/0110242 A1 | 5/2013 | Kirwan |
| 2013/0150968 A1 | 6/2013 | Dinville |
| 2013/0166029 A1 | 6/2013 | Dinville |
| 2013/0268076 A1 | 10/2013 | Carlson et al. |
| 2013/0310935 A1 | 11/2013 | Swann |
| 2013/0311093 A1 | 11/2013 | Winters et al. |
| 2013/0338776 A1 | 12/2013 | Jones |
| 2014/0074214 A1 | 3/2014 | Raje et al. |
| 2014/0074241 A1 | 3/2014 | McConnell |
| 2014/0088711 A1 | 3/2014 | Chin et al. |
| 2014/0114420 A1 | 4/2014 | Robinson |
| 2014/0148904 A1 | 5/2014 | Robinson |
| 2014/0180417 A1 | 6/2014 | Bergey |
| 2014/0194930 A1 | 7/2014 | Hess et al. |
| 2014/0236297 A1 | 8/2014 | Iott |
| 2014/0303731 A1 | 10/2014 | Glerum |
| 2014/0324171 A1 | 10/2014 | Glerum |
| 2014/0379085 A1 | 12/2014 | Duffield et al. |
| 2015/0012097 A1 | 1/2015 | Ibarra |
| 2015/0127107 A1* | 5/2015 | Kim ............... A61F 2/4611 623/17.16 |
| 2015/0202051 A1 | 7/2015 | Tanaka et al. |
| 2015/0209089 A1* | 7/2015 | Chataigner ........ A61F 2/4611 623/17.16 |
| 2015/0250603 A9 | 9/2015 | Glerum |
| 2015/0272743 A1 | 10/2015 | Jimenez et al. |
| 2015/0305880 A1 | 10/2015 | Kim et al. |
| 2015/0342754 A1 | 12/2015 | Geebelen et al. |
| 2016/0038845 A1 | 2/2016 | Mizunaga et al. |
| 2016/0058565 A1 | 3/2016 | Zappacosta et al. |
| 2016/0151171 A1 | 6/2016 | Mozeleski et al. |
| 2016/0338845 A1 | 11/2016 | Ashleigh |
| 2016/0374831 A1 | 12/2016 | Duffield et al. |
| 2017/0100260 A1 | 4/2017 | Duffield et al. |
| 2017/0165082 A1 | 6/2017 | Faulhaber |
| 2017/0165083 A1 | 6/2017 | Greenhalgh |
| 2017/0266016 A1 | 9/2017 | Faulhaber |
| 2017/0281358 A1 | 10/2017 | Wagner et al. |
| 2017/0296238 A1 | 10/2017 | Snell et al. |
| 2017/0303975 A1 | 10/2017 | Koch et al. |
| 2018/0104068 A1 | 4/2018 | Sack |
| 2018/0110627 A1 | 4/2018 | Sack |

FOREIGN PATENT DOCUMENTS

| | | |
|---|---|---|
| CN | 102596109 | 7/2012 |
| CN | 104822332 | 8/2015 |
| CN | 105188580 | 12/2015 |
| CN | 105250056 | 1/2016 |
| EP | 2389902 | 11/2011 |
| JP | 2015501189 A | 1/2015 |
| JP | 2016524988 A | 8/2016 |
| WO | 2010/092893 A1 | 8/2010 |
| WO | 2010092893 | 8/2010 |
| WO | 2011035126 | 3/2011 |
| WO | 2016210434 | 12/2016 |

OTHER PUBLICATIONS

International Search Report and Written Opinion dated Jan. 12, 2018 for International Patent Application No. PCT/US2017/56973.
International Search Report and Written Opinion dated Jan. 23, 2018 for International Patent Application No. PCT/US2017/058109.
International Search Report and Written Opinion dated Dec. 18, 2019 for International Patent Application No. PCT/US2019/47714.
Office Action dated Sep. 3, 2020 in JP Application No. 2019-520880.
Supplementary Partial European Search Report for EP 17 86 5409, dated Jun. 19, 2020 (17 pp).
Supplementary Partial European Search Report for EP 17 86 3072, dated Jun. 25, 2020 (17 pp).
Office Action dated Jun. 9, 2020 in U.S. Appl. No. 15/996,189.
Final Office Action dated Oct. 8, 2020 in U.S. Appl. No. 15/996,189.
Extended European Search Report dated Oct. 30, 2020 in EP 17865409.
Office Action dated Nov. 30, 2020 in CN 2017800805892.
Office Action dated Dec. 30, 2020 in CN 2017800781366.
Office Action dated Jun. 3, 2021 in JP 2019-520880.
Office Action dated Jun. 19, 2020 in EP 17885409.1.
Office Action dated Oct. 9, 2020 in EP 17885409.1.
Office Action dated Jun. 17, 2021 in CN 2017800805892.
Office Action dated Aug. 26, 2021 in U.S. Appl. No. 16/565,003.
Office Action dated Oct. 21, 2021 in U.S. Appl. No. 16/659,031.

* cited by examiner

IMPLANT WITH DEPLOYABLE BLADES

CROSS-REFERENCE TO RELATED APPLICATIONS

This application is a continuation of Sack, U.S. Pat. No. 10,307,265, issued Jun. 4, 2019, and entitled Implant with Deployable Blades, the entire disclosure of which is incorporated herein by reference.

BACKGROUND

The embodiments are generally directed to implants for supporting bone growth in a patient.

A variety of different implants are used in the body. Implants used in the body to stabilize an area and promote bone ingrowth provide both stability (i.e. minimal deformation under pressure over time) and space for bone ingrowth.

Spinal fusion, also known as spondylodesis or spondylosyndesis, is a surgical treatment method used for the treatment of various morbidities such as degenerative disc disease, spondylolisthesis (slippage of a vertebra), spinal stenosis, scoliosis, fracture, infection or tumor. The aim of the spinal fusion procedure is to reduce instability and thus pain.

In preparation for the spinal fusion, most of the intervertebral disc is removed. An implant, the spinal fusion cage, may be placed between the vertebra to maintain spine alignment and disc height. The fusion (i.e. bone bridge) occurs between the endplates of the vertebrae.

SUMMARY

In one aspect, an implant includes a body with a first axis. The implant also includes a blade having a retracted position in the body and an extended position where the blade extends outwardly from the body. The implant also includes a blade actuating member that can translate through the body in directions parallel to the first axis. The blade actuating member includes a channel, where the channel extends between a superior surface and an inferior surface of the blade actuating member, and where the channel defines a first channel direction and an opposing second channel direction. The blade includes a protruding portion configured to fit within the channel. When the blade actuating member is moved in a first direction along the first axis, the protruding portion follows the channel in the first channel direction and the blade moves towards the extended position. When the blade actuating member is moved in a second direction opposite the first direction, the protruding portion follows the channel in the second channel direction and the blade moves towards the retracted position.

In another aspect, an implant includes a body having a first axis. The implant also includes a blade having a retracted position in the body and an extended position where the blade extends outwardly from the body. The blade has an outer edge, an inner edge, a first lateral edge and a second lateral edge. The first lateral edge of the blade and the second lateral edge of the blade are in contact with the body. The blade also has a distal face and a proximal face. The implant includes a blade actuating member that can translate through the body in directions parallel to the first axis. A portion of the proximal face is in contact with the blade actuating member. The distal face is disposed away from the body. The blade actuating member can move the blade between the retracted position and the extended position.

In another aspect, an implant includes an outer structure having a first axis. The implant also includes a blade having a retracted position in the outer structure and an extended position where the blade extends outwardly from the outer structure. The implant also includes a blade actuating member that can translate through the outer structure in directions parallel to the first axis. The blade actuating member is coupled to the blade and can move the blade between the retracted position and the extended position. The outer structure includes a first end having a threaded opening and a guide opening adjacent the threaded opening, where the guide opening receives a driven end of the blade actuating member. The implant also includes a locking screw secured within the threaded opening. The locking screw can be rotated between an unlocked rotational position in which the driven end of the blade actuating member can pass through the guide opening and a locked rotational position, in which the drive end of the blade actuating member is prevented from moving through the guide opening.

Other systems, methods, features and advantages of the embodiments will be, or will become, apparent to one of ordinary skill in the art upon examination of the following figures and detailed description. It is intended that all such additional systems, methods, features and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, with emphasis instead being placed upon illustrating the principles of the embodiments. Moreover, in the figures, like reference numerals designate corresponding parts throughout the different views.

DETAILED DESCRIPTION

The embodiments described herein are directed to an implant for use in a spine. The embodiments include implants with a body and one or more blades. In addition to the various provisions discussed below, any embodiments may make use of any of the body/support structures, blades, actuating members or other structures disclosed in Duffield et al., U.S. Pat. No. 9,707,100, issued Jul. 18, 2017, and titled "Interbody Fusion Device and System for Implantation," which is hereby incorporated by reference in its entirety. For purposes of convenience, the Duffield patent will be referred to throughout the application as "The Fusion Device Application".

Introduction to the Implant

Figure 1:
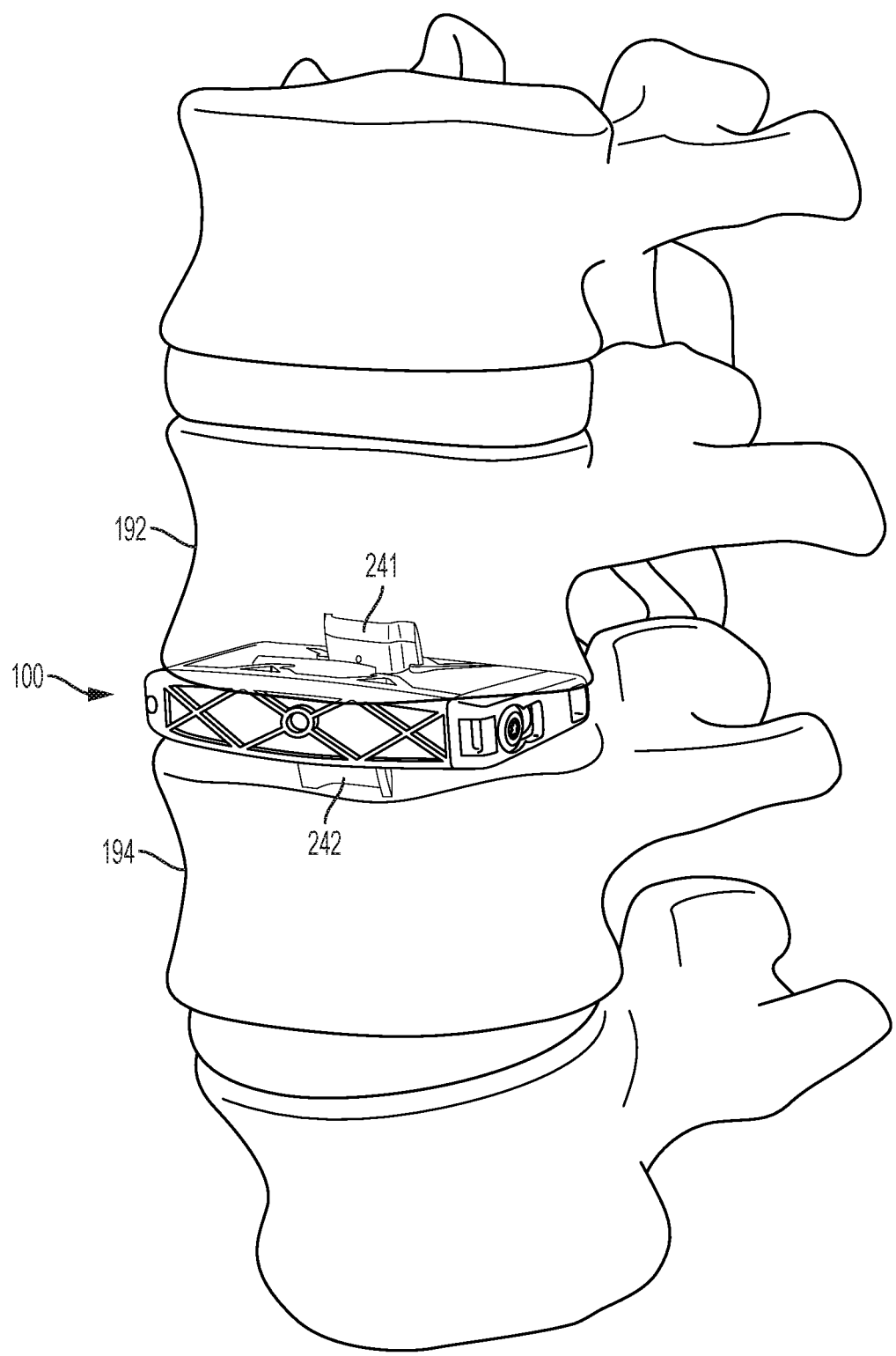
FIG. 1 is a schematic view of a spine with an implant, according to an embodiment.

FIG. 1 is a schematic view of an embodiment of an implant 100. Implant 100 may also be referred to as a cage or fusion device. In some embodiments, implant 100 is configured to be implanted within a portion of the human body. In some embodiments, implant 100 may be configured for implantation into the spine. In some embodiments, implant 100 may be a spinal fusion implant, or spinal fusion device, which is inserted between adjacent vertebrae to provide support and/or facilitate fusion between the vertebrae. For example, referring to FIG. 1, implant 100 has been positioned between a first vertebra 192 and a second vertebra 194. Moreover, implant 100 is seen to include two blades (first blade 241 and second blade 242), which extend from the superior and inferior surfaces of implant 100. Each of the blades has been driven into an adjacent vertebra (i.e., first vertebra 192 or second vertebra 194) so as to help anchor implant 100.

In some embodiments, implant 100 may be inserted using a lateral interbody fusion (LIF) surgical procedure. In some cases, implant 100 could be inserted through a small incision in the side of the body. Exemplary techniques that could be used include, but are not limited to: DLIF® (Direct Lateral Interbody Fusion), XLIF® (eXtreme Lateral Interbody Fusion), and transpsoas interbody fusion.

For purposes of clarity, reference is made to various directional adjectives throughout the detailed description and in the claims. As used herein, the term "anterior" refers to a side or portion of an implant that is intended to be oriented towards the front of the human body when the implant has been placed in the body. Likewise, the term "posterior" refers to a side or portion of an implant that is intended to be oriented towards the back of the human body following implantation. In addition, the term "superior" refers to a side or portion of an implant that is intended to be oriented towards a top (e.g., the head) of the body while "inferior" refers to a side or portion of an implant that is intended to be oriented towards a bottom of the body. Reference is also made herein to "lateral" sides or portions of an implant, which are sides or portions facing along a lateral direction of the body.

Figure 2:
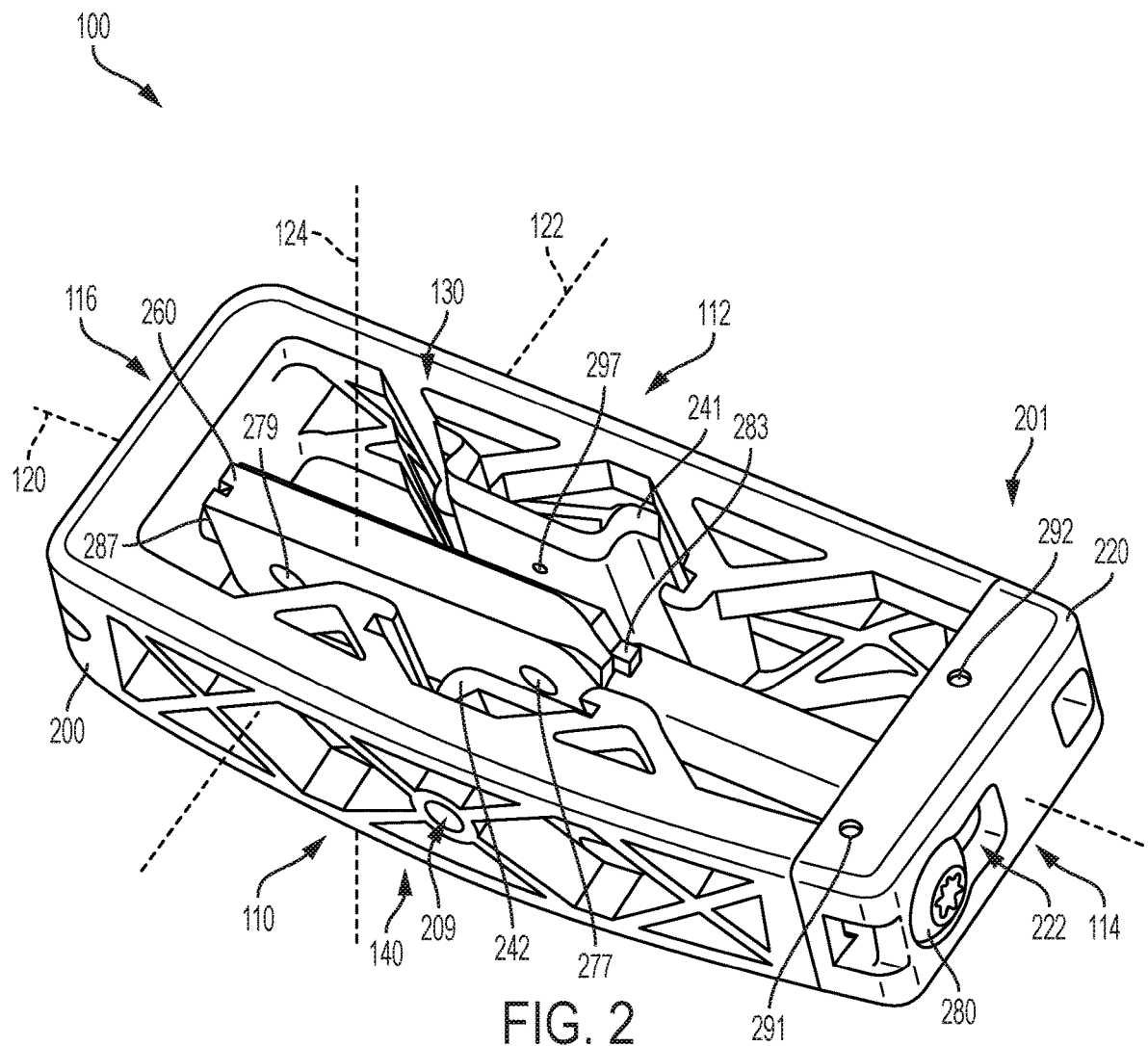
FIG. 2 is an isometric view of an embodiment of an implant.

FIG. 2 is a schematic isometric view of an embodiment of implant 100, according to an embodiment. As seen in FIG. 2, implant 100 is understood to be configured with an anterior side 110 and a posterior side 112. Implant 100 may also include a first lateral side 114 and a second lateral side 116. Furthermore, implant 100 may also include a superior side 130 and an inferior side 140.

Reference is also made to directions or axes that are relative to the implant itself, rather than to its intended orientation with regards to the body. For example, the term "distal" refers to a part that is located further from a center of an implant, while the term "proximal" refers to a part that is located closer to the center of the implant. As used herein, the "center of the implant" could be the center of mass and/or a central plane and/or another centrally located reference surface.

An implant may also be associated with various axes. Referring to FIG. 1, implant 100 may be associated with a longitudinal axis 120 that extends along the longest dimension of implant 100 between first lateral side 114 and second lateral side 116. Additionally, implant 100 may be associated with a posterior-anterior axis 122 (also referred to as a "widthwise axis") that extends along the widthwise dimension of implant 100, between posterior side 112 and anterior side 110. Moreover, implant 100 may be associated with a vertical axis 124 that extends along the thickness dimension of implant 100 and which is generally perpendicular to both longitudinal axis 120 and posterior-anterior axis 122.

An implant may also be associated with various reference planes or surfaces. As used herein, the term "median plane" refers to a vertical plane which passes from the anterior side to the posterior side of the implant, dividing the implant into right and left halves, or lateral halves. As used herein, the term "transverse plane" refers to a horizontal plane located in the center of the implant that divides the implant into superior and inferior halves. As used herein, the term "coronal plane" refers to a vertical plane located in the center of the implant that divides the implant into anterior and posterior halves. In some embodiments, the implant is symmetric about two planes, such as the median and the transverse plane.

Figure 3:
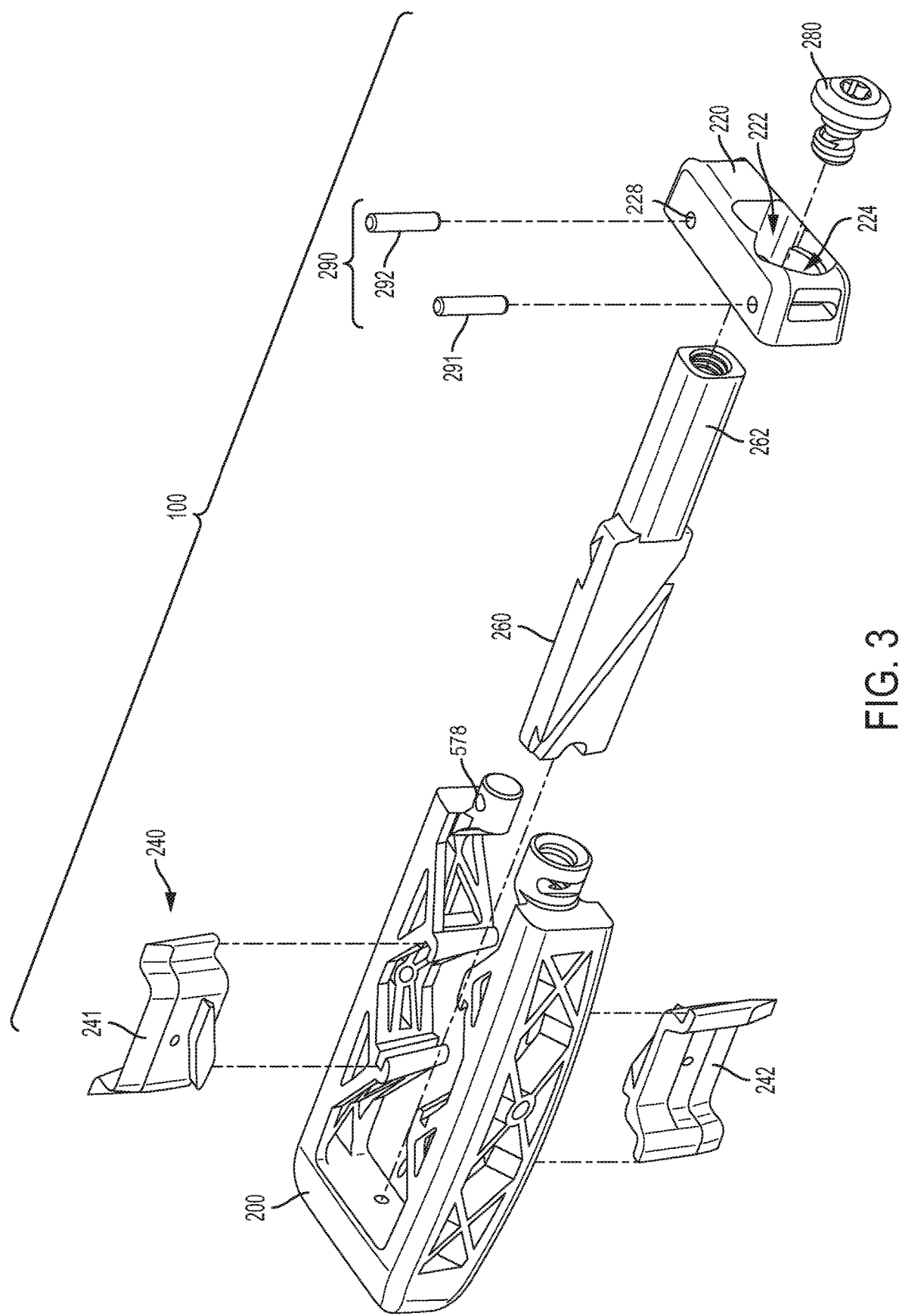
FIG. 3 is an exploded isometric view of the implant of FIG. 2.

FIG. 3 is a schematic isometric exploded view of implant 100 according to an embodiment. Referring first to FIGS. 2-3, implant 100 is comprised of a body 200 and a cap 220, which together may be referred to as outer structure 201 of implant 100. In some embodiments, a body and cap may be integrally formed. In other embodiments, a body and cap may be separate pieces that are joined by one or more fasteners. In the embodiment of FIGS. 2-3, body 200 and cap 220 are separate pieces that are fastened together using additional components of implant 100.

Embodiments of an implant may include provisions for anchoring the implant into adjacent vertebral bodies. In some embodiments, an implant may include one or more anchoring members. In the embodiment of FIGS. 2-3, implant 100 includes a set of blades 240 that facilitate anchoring implant 100 to adjacent vertebral bodies following insertion of implant 100 between the vertebral bodies. Set of blades 240 may be further comprised of a first blade 241 and a second blade 242. Although the exemplary embodiments described herein include two blades, other embodiments of an implant could include any other number of blades. For example, in another embodiment, three blades could be used. In another embodiment, four blades could be used, with two blades extending from the inferior surface and two blades extending from the superior surface of the implant. Still other embodiments could include five or more blades. In yet another embodiment, a single blade could be used.

An implant with blades can include provisions for moving the blades with respect to an outer structure of the implant. In some embodiments, an implant includes a blade actuating member that engages with one or more blades to extend and/or retract the blades from the surfaces of the implant. In the embodiment shown in FIGS. 2-3, implant 100 includes a blade actuating member 260. In some embodiments, blade actuating member 260 is coupled to first blade 241 and second blade 242. Moreover, by adjusting the position of blade actuating member 260 within outer structure 201, first blade 241 and second blade 242 can be retracted into, or extended from, surfaces of implant 100.

An implant can include provisions for locking the position of one or more elements of the implant. In embodiments where the position of a blade actuating member can be changed, an implant can include provisions for locking the actuating member in a given position, thereby also locking one or more blades in a given position. In the embodiment shown in FIGS. 2-3, implant 100 includes locking screw 280. In some embodiments, locking screw 280 can be used to lock blade actuating member 260 in place within implant 100, which ensures first blade 241 and second blade 242 remain in an extended position.

Embodiments can include one or more fasteners that help attach a body to a cap. In some embodiments, pins, screws, nails, bolts, clips, or any other kinds of fasteners could be used. In the embodiment shown in FIGS. 2-3, implant 100 includes a set of pins 290 that help fasten cap 220 to body 200. In the exemplary embodiments, two pins are used, including first pin 291 and second pin 292. In other embodiments, however, any other number of pins could be used. In another embodiment, a single pin could be used. In still other embodiments, three or more pins could be used.

Operation

The embodiments described herein provide an implant that can move from a first position (the "insertion position"), which allows the implant to maintain a low profile, to a second position (the "impaction position" or the "deployed position"), that deploys the blades and inserts them into the proximal superior and inferior vertebral bodies. While the implant is in the first (insertion) position, the blades of the device may be retracted within the body of the implant (i.e., the blades may themselves be in a "retracted position"). In the second (deployed) position of the implant, the blades extend superiorly (or cranially) or inferiorly (or caudally) beyond the implant and into the vertebral bodies to prevent the implant from moving out of position over time. Thus, the blades themselves may be said to be in an "extended position" or "deployed position". When the blades are deployed, the implant resists left to right rotation and resists flexion and/or extension. It may be appreciated that although the blades may approximately move in vertical directions (i.e., the superior and inferior directions), the actual direction of travel may vary from one embodiment to another. For example, in some embodiments the blades may be slightly angled within the implant and may deploy at slight angles to a vertical direction (or to the inferior/superior directions).

Figure 4:
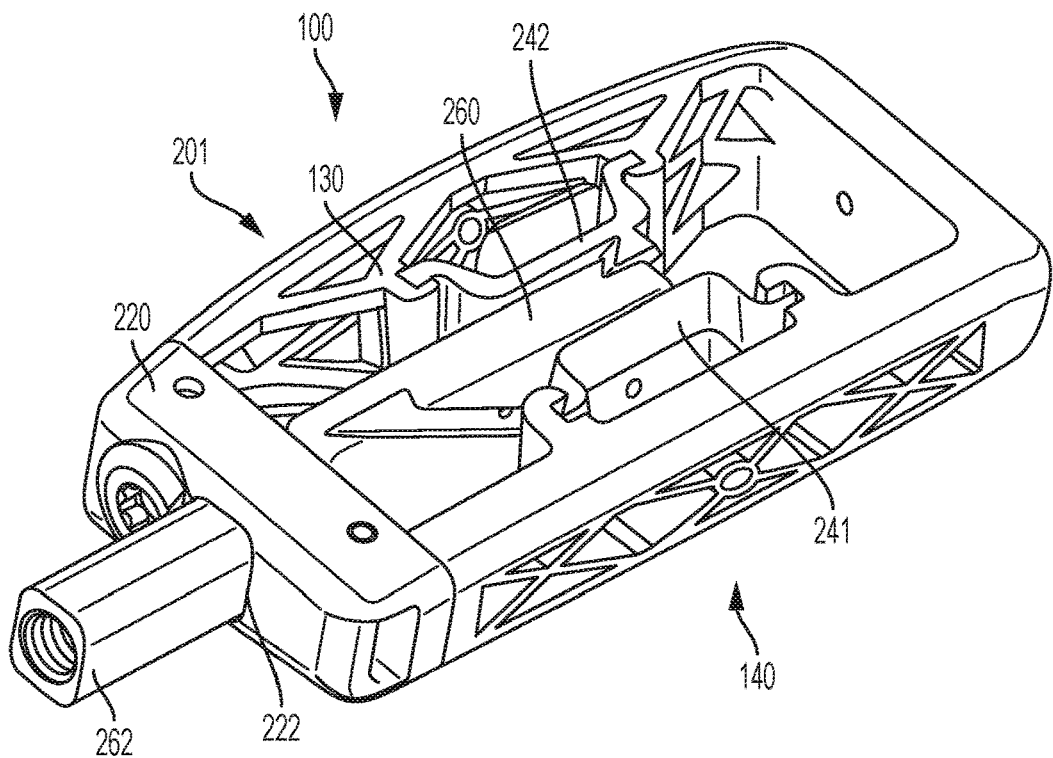
FIG. 4 is a schematic isometric view of the implant of FIG. 2 in an insertion position.
Figure 5:
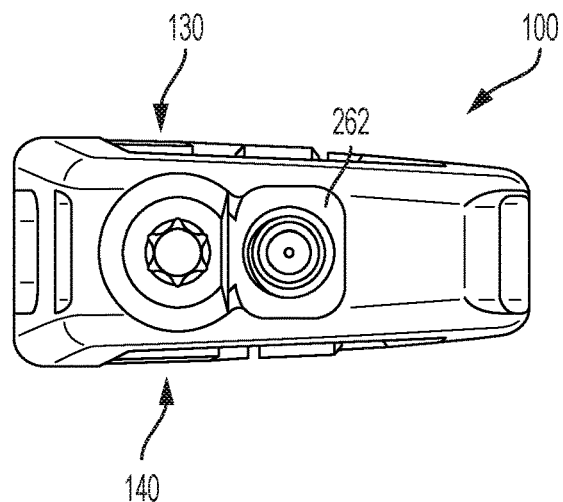
FIG. 5 is a lateral side view of the implant of FIG. 2 in the insertion position.

FIGS. 4-7 illustrate several views of implant 100 in different operating modes or operating positions. Specifically, FIG. 4 is a schematic isometric view of implant 100 in an insertion position. FIG. 5 is a schematic lateral side view of implant 100 in the same insertion position of FIG. 4. Referring to FIGS. 4-5, in the insertion position driven end 262 of blade actuating member 260 may be disposed distal to guide opening 222 of cap 220 (i.e., a portion of blade actuating member 260 is disposed through guide opening 222). With implant 100 in the insertion position, first blade 241 and second blade 242 are retracted within outer structure 201. Thus, as best seen in FIG. 5, neither first blade 241 or second blade 242 extend outwardly (distally) from superior side 130 or inferior side 140, respectively, of implant 100. In this insertion position, implant 100 has a compact profile and can be more easily maneuvered into place in the excised disc space between adjacent vertebrae.

Figure 6:
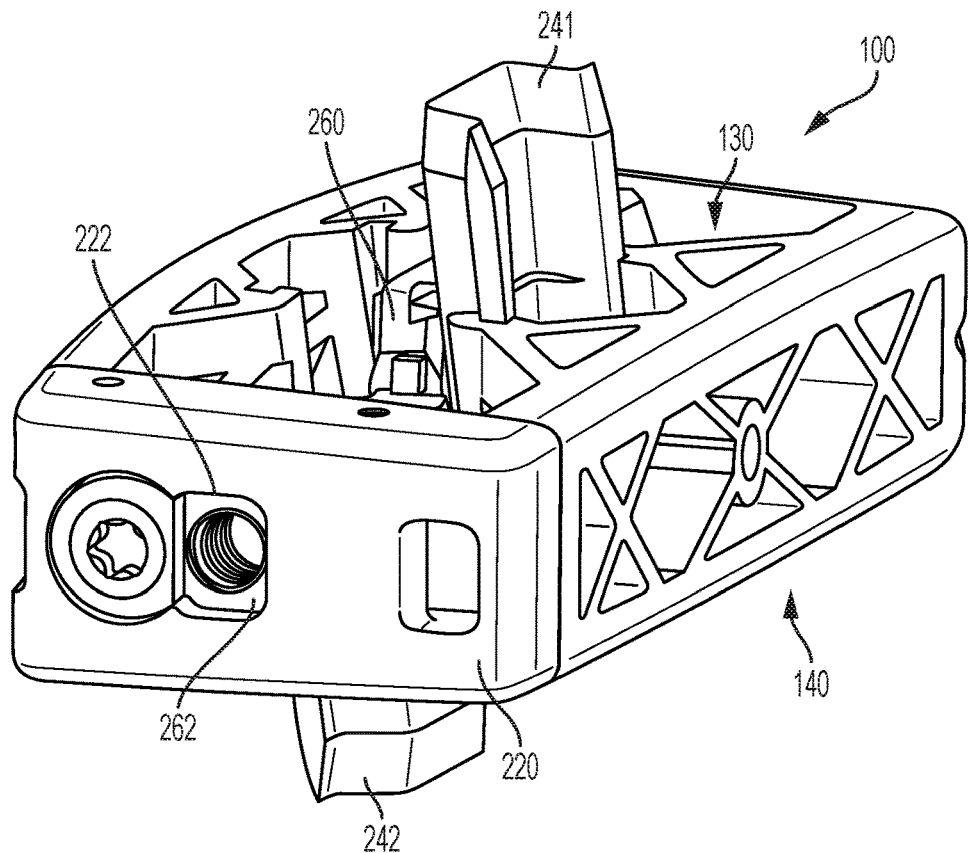
FIG. 6 is a schematic isometric view of the implant of FIG. 2 in a deployed position.
Figure 7:
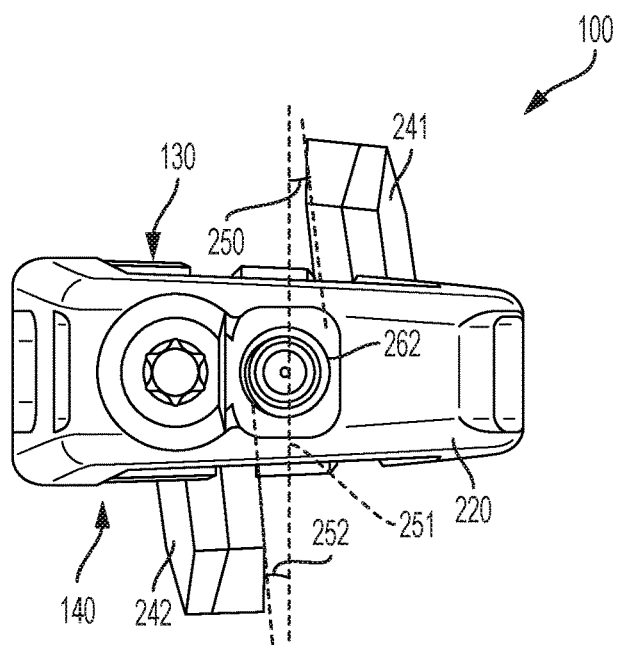
FIG. 7 is a lateral side view of the implant of FIG. 2 in the deployed position.

FIG. 6 is a schematic isometric view of implant 100 in a deployed position. FIG. 7 is a schematic lateral side view of implant 100 in the same insertion position of FIG. 7. Referring to FIGS. 6-7, in the deployed position driven end 262 of blade actuating member 260 may be disposed proximally to guide opening 222 of cap 220 (i.e., the entirety of blade actuating member 260 is disposed within implant 100). With implant 100 in the deployed position, first blade 241 and second blade 242 are extended outwards from superior side 130 and inferior side 140, respectively, so as to be inserted into adjacent vertebral bodies.

In some embodiments, one or more blades could be deployed at a slight angle, relative to the normal directions on the superior and inferior surfaces of the implant. In some embodiments, one or more blades could be oriented at an angle between 0 and 30 degrees. In other embodiments, one or more blades could be oriented at an angle that is greater than 30 degrees. In the exemplary embodiment shown in FIGS. 6-7, first blade 241 and second blade 242 are both oriented at a slight angle from normal axis 251. Specifically, first blade 241 forms a first angle 250 with normal axis 251 and second blade 242 forms a second angle 252 with normal axis 251. In one embodiment, first angle 250 and second angle 252 are both approximately 15 degrees. Angling the blades in this way may help keep first blade 241 and second blade 242 approximately centered in the adjacent vertebrae upon deployment.

The extension of each blade could vary in different embodiments. In some embodiments, a blade could extend outwardly by a length between 0 and 100% of the depth of an implant. In still other embodiments, combined blade height could extend outwardly by a length between 100 and 130% of the depth of an implant. In the exemplary embodiment shown in FIGS. 6-7, first blade 241 and second blade 242 combined may be capable of extending outwardly from implant 100 by an amount equal to 110% of the depth of implant 100. This can be done while still keeping the blades fully retracted within implant 100 since the blades are guided by two robust parallel tracks in body 200 and also by angled cross channels in blade actuating member 260, thus constraining all six axes of motion. In other embodiments, the combined blade height at deployment could be less than 100%. In one embodiment, the implant could be designed so that the combined blade height is less than 10 mm to reduce the risk of fracturing the adjacent vertebral bodies.

Blades and Blade Actuating Member

Figure 8:
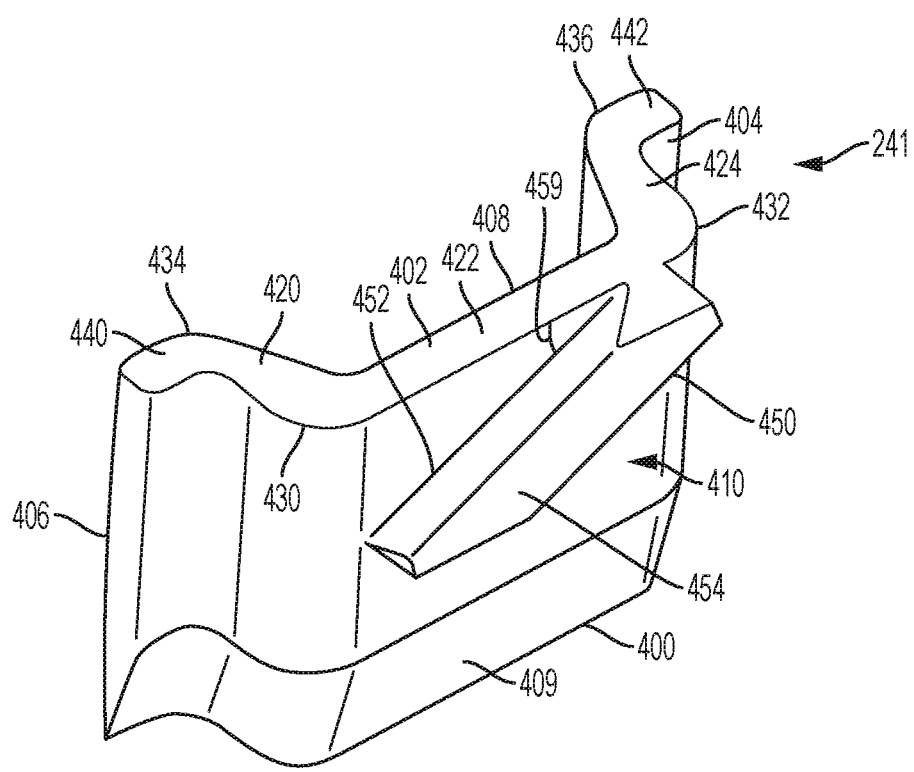
FIG. 8 is a schematic isometric view of an embodiment of a blade.

FIG. 8 is a schematic isometric view of first blade 241. First blade 241, or simply blade 241, includes an outer edge 400, an inner edge 402, a first lateral edge 404 and a second lateral edge 406. These edges bind a distal face 408 (i.e., a face oriented in the distal direction) and a proximal face 410 (i.e., a face oriented in the proximal direction).

In different embodiments, the geometry of a blade could vary. In some embodiments, a blade could have a substantially planar geometry such that the distal face and the proximal face of the blade are each parallel with a common plane. In other embodiments, a blade could be configured with one or more bends. In some embodiments, a blade can have a channel-like geometry (ex. "C"-shaped or "S"-shaped). In the embodiment shown in FIG. 8, blade 241 has a U-shaped geometry with flanges. In particular, blade 241 a first channel portion 420, a second channel portion 422 and a third channel portion 424. Here, the first channel portion 420 is angled with respect to second channel portion 422 at a first bend 430. Likewise, third channel portion 424 is angled with respect to second channel portion 422 at second bend 432. Additionally, blade 241 includes a first flange 440 extending from first channel portion 420 at a third bend 434. Blade 241 also includes second flange 442 extending from third channel portion 424 at fourth bend 436. This geometry for blade 241 helps provide optimal strength for blade 241 compared to other planar blades of a similar size and thickness, and allowing for greater graft volume.

In the exemplary embodiment, the outer edge 400 is a penetrating edge configured to be implanted within an adjacent vertebral body. To maximize penetration, outer edge 400 may be sharpened so that blade 241 has an angled surface 409 adjacent outer edge 400. Moreover, in some embodiments, first lateral edge 404 and second lateral edge 406 are also sharpened in a similar manner to outer edge 400 and may act as extensions of outer edge 400 to help improve strength and penetration.

A blade can include provisions for coupling with a blade actuating member. In some embodiments, a blade can include a protruding portion. In some embodiments, the protruding portion can extend away from a face of the blade and may fit within a channel in a blade actuating member. Referring to FIG. 8, blade 241 includes a protruding portion 450 that extends from proximal face 410. Protruding portion 450 may generally be sized and shaped to fit within a channel of blade actuating member 260 (i.e., first channel 350 shown in FIG. 9). In particular, the cross-sectional shape may fit within a channel in blade actuating member 260. In some cases, the cross-sectional width of protruding portion 450 may increase between a proximal portion 452 and a distal portion 454 allowing protruding portion 450 to be interlocked within a channel as discussed in detail below.

Figure 9:
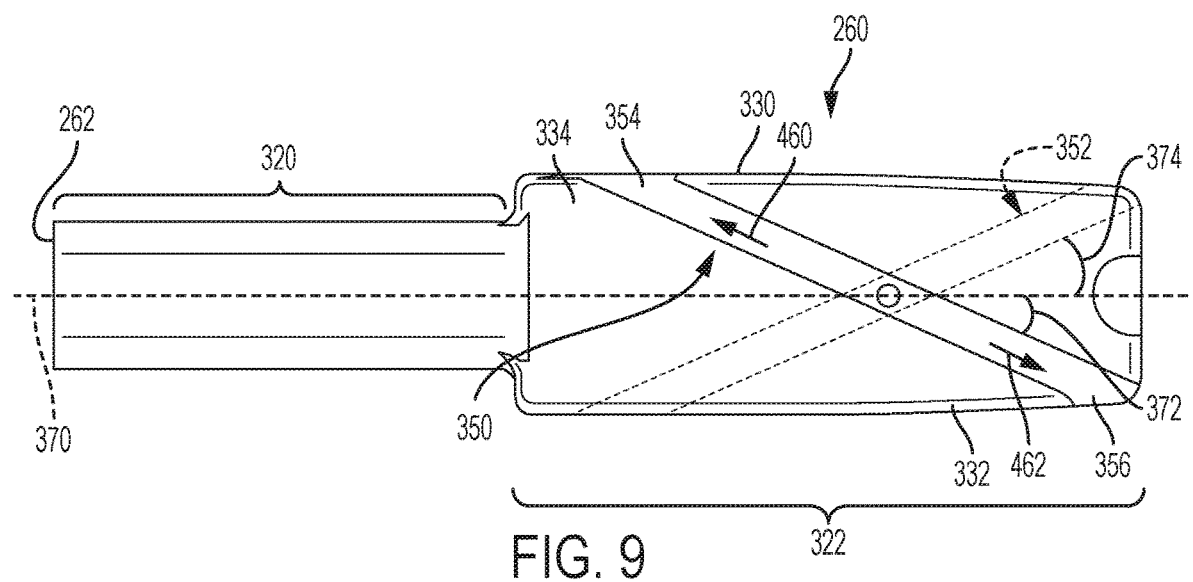
FIG. 9 is a schematic side view of an embodiment of a blade actuating member.

A protruding portion may be oriented at an angle on a blade so as to fit with an angled channel in a blade actuating member. In the embodiment of FIG. 9, protruding portion 450 may be angled with respect to inner edge 402 such that blade 241 is vertically oriented within implant 100 when protruding portion 450 is inserted within first channel 350. In other words, the longest dimension of protruding portion 450 may form an angle 459 with inner edge 402.

Although the above discussion is directed to first blade 241, it may be appreciated that similar principles apply for second blade 242. In particular, in some embodiments, second blade 242 may have a substantially identical geometry to first blade 241.

Figure 10:
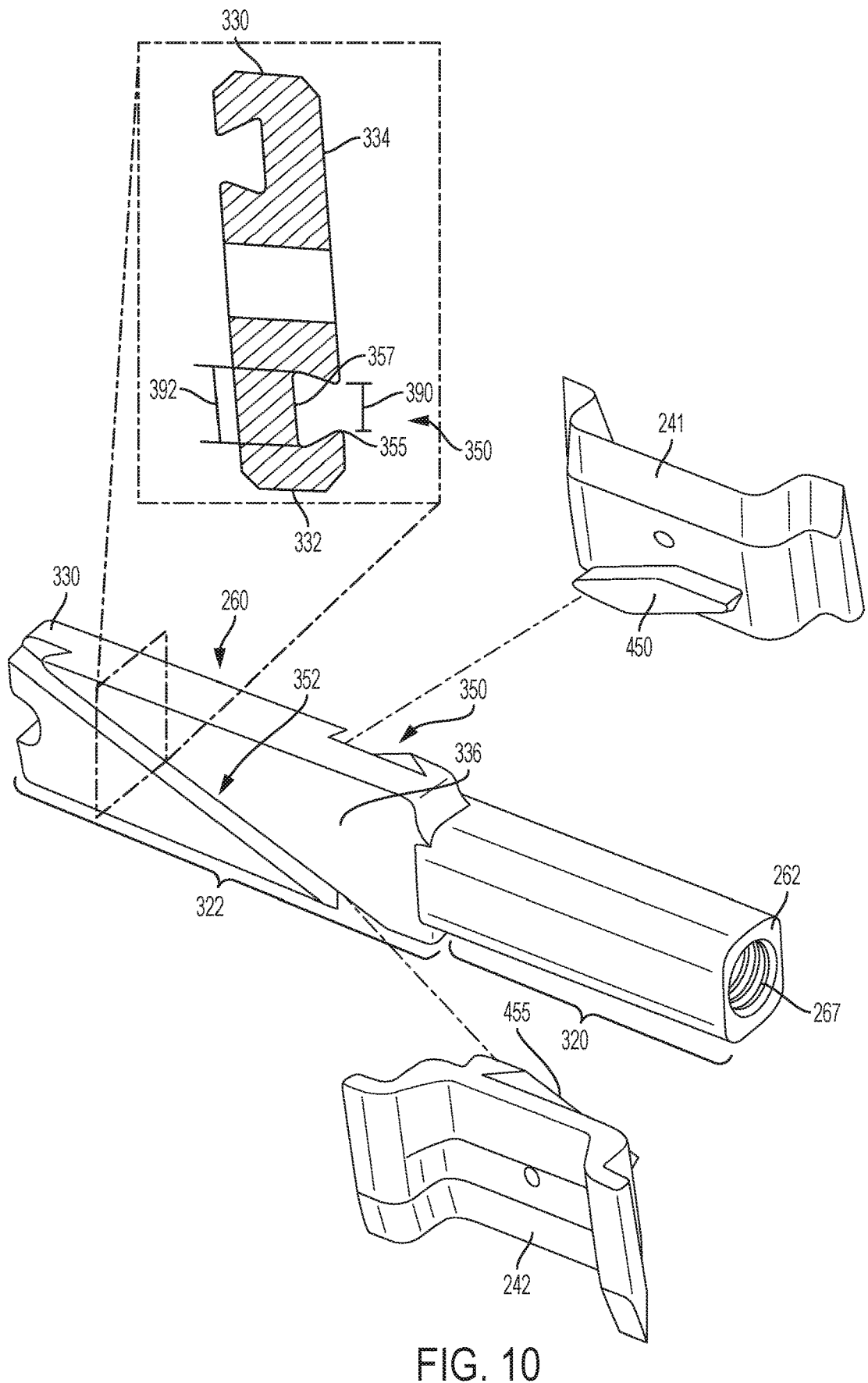
FIG. 10 is a schematic isometric view of an embodiment of a blade actuating member and two corresponding blades.

FIG. 9 is a schematic side view of an embodiment of blade actuating member 260. An isometric view of blade actuating member 260 is also shown in FIG. 10. Referring to FIGS. 9 and 10, blade actuating member 260 may include a driven shaft portion 320 and a blade engaging portion 322. Driven shaft portion 320 further includes driven end 262.

In some embodiments, driven end 262 can include one or more engaging features. For example, driven end 262 can include a threaded opening 267, as best seen in FIG. 10. In some embodiments, threaded opening 267 may receive a tool with a corresponding threaded tip. With this arrangement, driven end 262 can be temporarily mated with the end of a tool used to impact blade actuating member 260 and drive set of blades 240 into adjacent vertebrae. This may help keep the driving tool and driven end 262 aligned during the impact and reduce any tendency of the driving tool to slip with respect to driven end 262. Using mating features also allows driven end 262 to be more easily "pulled" distally from implant 100, which can be used to retract blades 240, should it be necessary to remove implant 100 or re-position the blades.

Blade engaging portion 322 may comprise a superior surface 330, an inferior surface 332, a first side surface 334 and a second side surface 336. Here, first side surface 334 may be an anterior facing side and second side surface 336 may be a posterior facing side. In other embodiments, however, first side surface 334 could be a posterior facing side and second side surface 336 could be an anterior facing side.

A blade actuating member can include provisions for coupling with one or more blades. In some embodiments, a blade actuating member can include one or more channels. In the exemplary embodiment of FIG. 9, blade engaging portion 322 includes a first channel 350 and a second channel 352 (shown in phantom in FIG. 9). First channel 350 may be disposed in first side surface 334 of blade actuating member 260 while second channel 352 may be disposed in second side surface 336 of blade actuating member 260.

Each channel is seen to extend at an angle between superior surface 330 and inferior surface 332 of a blade engaging portion 322. For example, as best seen in FIG. 9, first channel 350 has a first end 354 open along superior surface 330 and a second end 356 open along inferior surface 332. Moreover, first end 354 is disposed closer to driven shaft portion 320 than second end 356. Likewise, second channel 352 includes opposing ends on superior surface 330 and inferior surface 332, though in this case the end disposed at superior surface 330 is disposed further from driven shaft portion 320 than the end disposed at inferior surface 332.

In different embodiments, the angle of each channel could be selected to provide proper blade extension for varying implant sizes. As used herein, the angle of a channel is defined to be the angle formed between the channel and a transverse plane of the blade actuating member. In the embodiment of FIG. 9, first channel 350 forms a first angle 372 with transverse plane 370 of blade actuating member 260, while second channel 352 forms a second angle 374 with transverse plane 370. In the exemplary embodiment, first angle 372 and second angle 374 are equal to provide balanced reactive forces as the blades are deployed. By configuring the blades and blade actuating member in this manner, each blade is deployed about a centerline (e.g., transverse plane 370) of the blade actuating member, which helps minimize friction and binding loads between these parts during blade deployment. Additionally, the arrangement helps provide balanced reaction forces to reduce insertion effort and friction.

In different embodiments, the angle of each channel could vary. In some embodiments, a channel could be oriented at any angle between 15 and 75 degrees. In other embodiments, a channel could be oriented at any angle between 35 and 65 degrees. Moreover, in some embodiments, the angle of a channel may determine the angle of a protruding portion in a corresponding blade. For example, the angle 459 formed between protruding portion 450 and inner edge 402 of blade 241 (see FIG. 8) may be approximately equal to the angle 372 formed between first channel 350 and transverse plane 370. This keeps the outer penetrating edge of blade 241 approximately horizontal so that the degree of penetration does not vary at different sections of the blade.

As seen in FIG. 10, each channel has a cross-sectional shape that facilitates a coupling or fit with a corresponding portion of a blade. As an example, channel 350 has an opening 355 on first side surface 334 with an opening width 390. At a location 357 that is proximal to opening 355, channel 350 has a width 392 that is greater than opening width 390. This provides a cross-sectional shape for channel 350 that allows for a sliding joint with a corresponding part of first blade 241. In the exemplary embodiment, first channel 350 and second channel 352 are configured with dovetail cross-sectional shapes. In other embodiments, however, other various cross-sectional shapes could be used that would facilitate a similar sliding joint connection with a correspondingly shaped part. In other words, in other embodiments, any geometry for a blade and a blade actuating member could be used where the blade and blade actuating member include corresponding mating surfaces of some kind.

In some embodiments, blade engaging portion 322 may be contoured at the superior and inferior surfaces to resist subsidence and allow maximum blade deployment depth. This geometry may also help to keep the blade engaging portion 322 centered between vertebral endplates. As an example, the contouring of superior surface 330 and inferior surface 332 in the present embodiment is best seen in the enlarged cross-sectional view of FIG. 10.

Figure 11:
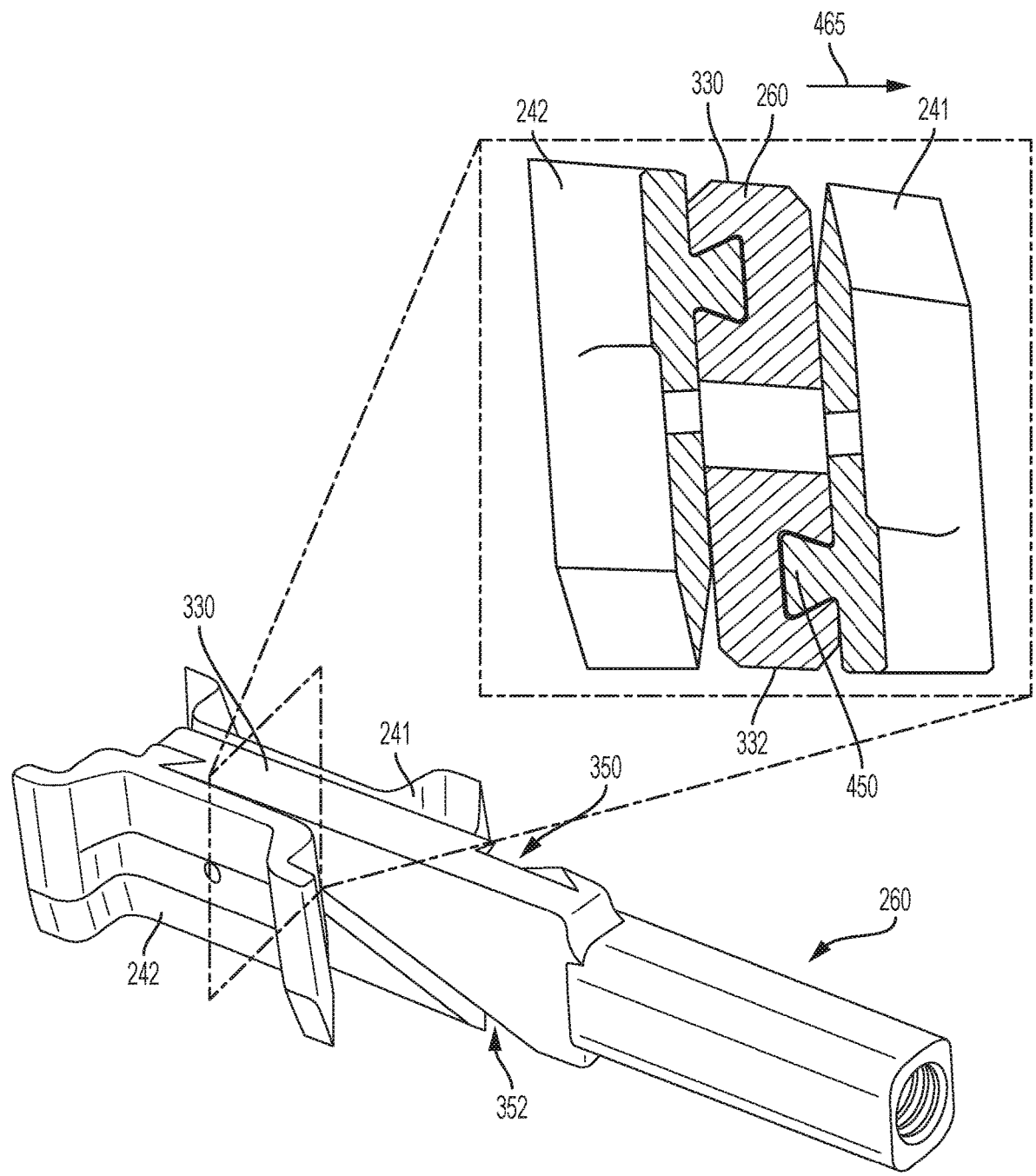
FIG. 11 is a schematic isometric view of the blade actuating member of FIG. 10 coupled with the two corresponding blades.

FIGS. 10-11 illustrate a schematic exploded isometric view and a schematic view, respectively, of blade actuating member 260 and set of blades 240. Referring to FIGS. 10-11, protruding portion 450 of first blade 241 fits into first channel 350. Likewise, protruding portion 455 of second blade 242 fits into second channel 352.

Each channel may be associated with a first channel direction and an opposing second channel direction. For example, as best seen in FIG. 9, first channel 350 may be associated with a first channel direction 460 that is directed towards superior surface 330 along the length of first channel 350. Likewise, first channel 350 includes a second channel direction 462 that is directed towards inferior surface 332 along the length of first channel 350.

With first protruding portion 450 of first blade 241 disposed in first channel 350, first protruding portion 450 can slide in first channel direction 460 or second channel direction 462. As first protruding portion 450 slides in first channel direction 460, first blade 241 moves vertically with respect to blade actuating member 260 such that first blade 241 extends outwardly on a superior side of implant 100 (see FIGS. 6-7). As first protruding portion 450 slides in second channel direction 462, first blade 241 moves vertically with respect to blade actuating member 260 such that first blade 241 is retracted within outer structure 201 of implant 100 (see FIGS. 4-5). In a similar manner, second protruding portion 455 of second blade 242 may slide in first and second channel directions of second channel 352 such that second blade 242 can be extended and retracted from implant 100 on an inferior side (see FIGS. 4-7). By using this configuration, blade actuating member 260 propels both blades in opposing directions thereby balancing the reactive loads and minimizing cantilevered loads and friction on the guide bar.

As shown in the cross section of FIG. 11, the fit between each blade and the respective channel in blade actuating member 260 may be configured to resist motion in directions orthogonal to the corresponding channel directions. For example, with first protruding portion 450 inserted within first channel 350, first blade 241 can translate along first channel direction 460 or second channel direction 462, but may not move in a direction 465 that is perpendicular to first channel direction 460 and second channel direction 462 (i.e., blade 241 cannot translate in a direction perpendicular to the length of first channel 350). Specifically, as previously mentioned, the corresponding cross-sectional shapes of first channel 350 and first protruding portion 450 are such that first protruding portion 450 cannot fit through the opening in first channel 350 on first side surface 334 of blade actuating member 260.

In some embodiments, each protruding portion forms a sliding dovetail connection or joint with a corresponding channel. Using dovetail tracks on the blade actuating member and corresponding dovetail features on the posterior and anterior blades allows axial movement along the angle of inclination while preventing disengagement under loads encountered during blade impaction and retraction. For example, in FIG. 11, first protruding portion 450 forms a sliding dovetail joint with first channel 350. Of course, the embodiments are not limited to dovetail joints and other fits/joints where the opening in a channel is smaller than the widest part of a protruding portion of a blade could be used.

It may be appreciated that in other embodiments, the geometry of the interconnecting parts between a blade and a blade actuating member could be reversed. For example, in another embodiment, a blade could comprise one or more channels and a blade actuating member could include corresponding protrusions to fit in the channels. In such embodiments, both the protruding portion of the blade actuating member and the channels in the blades could have corresponding dovetail geometries.

Body and Cap

Figure 12:
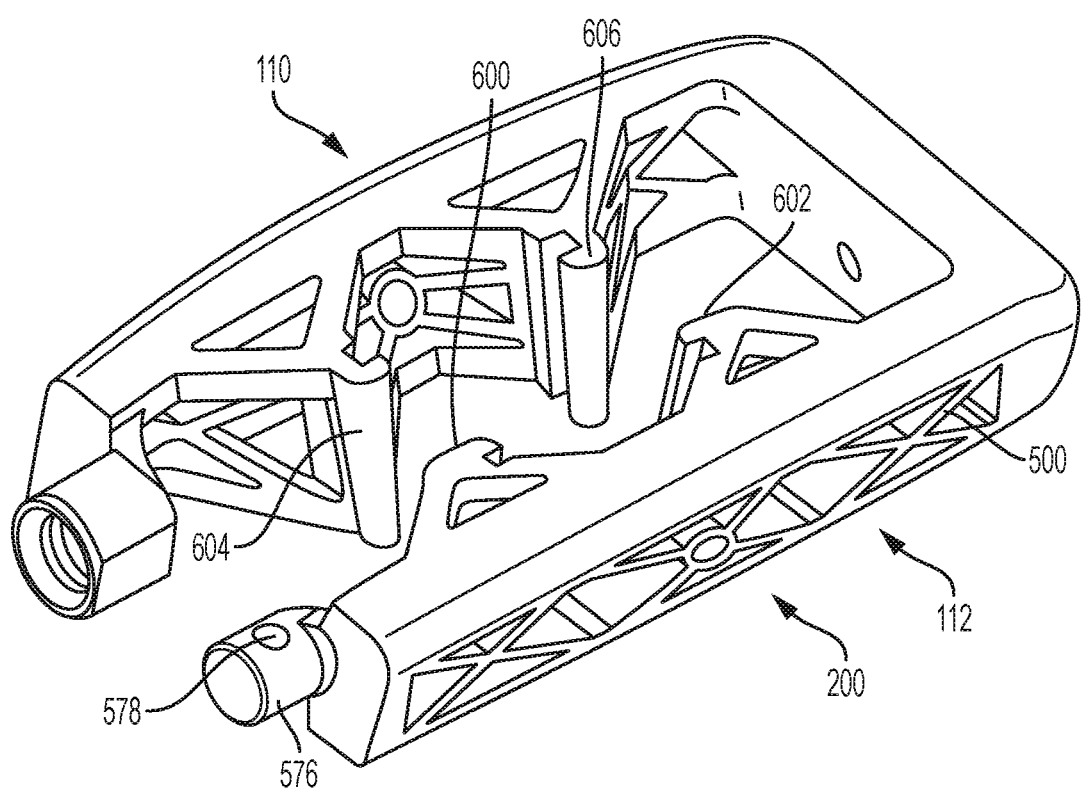
FIG. 12 is a schematic isometric view of an embodiment of a body for an implant.

FIG. 12 illustrates a schematic view of body 200. Body 200 may provide the posterior and anterior sides of outer structure 201, as well as at least one lateral side of outer structure 201.

In some embodiments, the posterior and anterior sides of a body may both have a truss-like or lattice-like geometry. In other embodiments, the posterior and/or anterior sides could be configured as solid walls with one or more openings. In the exemplary embodiment shown in FIG. 12, posterior side 112 and anterior side 110 of body 200 have a truss-like geometry comprised of diagonally oriented supports 500. Although a particular pattern of supports is shown in FIG. 12, other embodiments could have supports arranged in any other pattern, including any truss-like and/or lattice-like patterns.

The configuration of supports 500 shown for the embodiment of FIG. 12 may facilitate the manufacturing process. In particular, this configuration may permit 3D Printing via laser or electron beam with minimal support structures by orienting the diagonal supports 500 more than 45 degrees in relation to the build direction. Although the embodiment of FIG. 12 uses a truss-structure with openings between supports, other embodiments could include thin walls of material to fill in some of the openings between supports. Using an open truss design and/or a truss design with thin walls may help to improve visibility of adjacent bony anatomy under X-ray fluoroscopy while still providing sufficient structural support and rigidity to withstand all testing requirements and the clinical loading of an implant.

Figure 15:
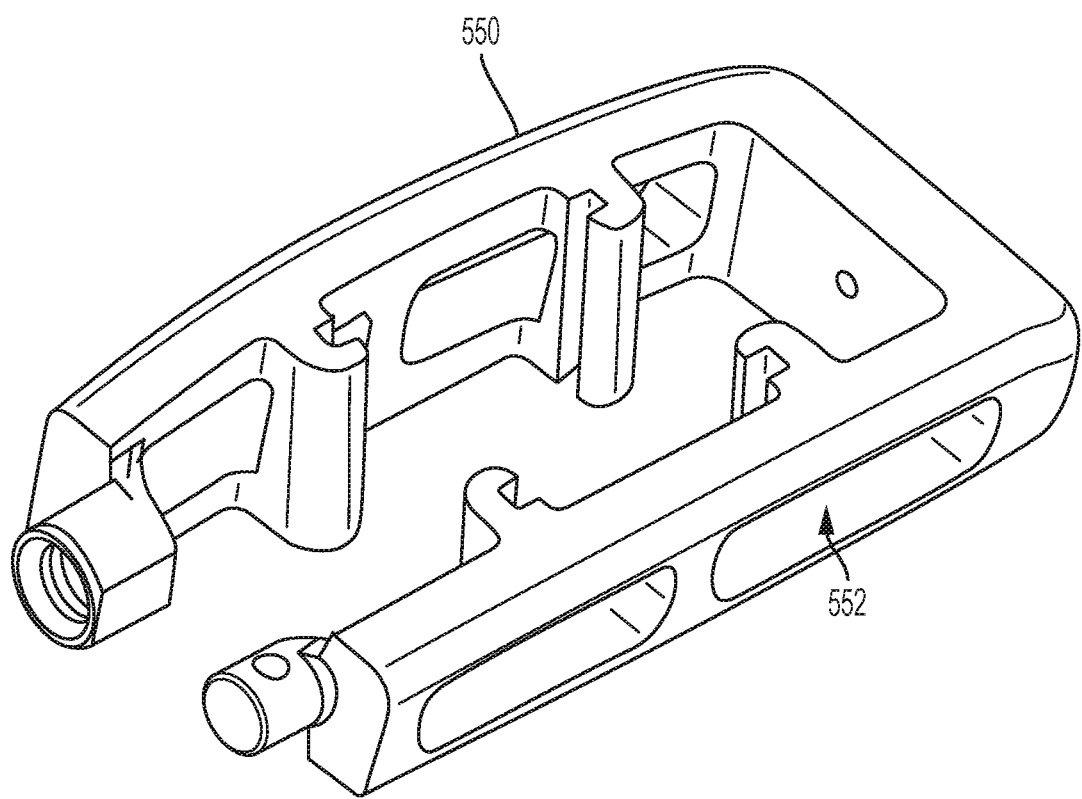
FIG. 15 is a schematic isometric view of body for an implant, according to another embodiment.

In other embodiments, a body may not have a truss or lattice-like geometry. For example, an alternative design for a body 550 is shown in FIG. 15. As seen in FIG. 15, body 550 may be similar to body 200 in some respects. However, rather than having a truss-like geometry, body 550 uses a solid geometry with oval-shaped openings 552 on both the anterior and posterior sides. Other embodiments, not pictured in the figures, include round or rectangular openings in otherwise solid geometry of the anterior, posterior, or lateral sides.

Embodiments can also include one or more blade retaining portions. A blade retaining portion may receive any part of a blade, including one or more edges and/or faces of the blade. In one embodiment, a body includes blade retaining portions to receive the lateral edges of each blade. As seen in FIG. 12, body 200 includes a first blade retaining portion 600 and a second blade retaining portion 602 on posterior side 112. First blade retaining portion 600 is comprised of a first blade retaining channel extending through the depth of body 200 that receives first lateral edge 404 of first blade 241 (see FIG. 8). Likewise, second blade retaining portion 602 is comprised of a second blade retaining channel extending through the depth of body 200 that receives second lateral edge 406 of first blade 241 (see FIG. 8). Body 200 also includes third blade retaining portion 604 and fourth retaining portion 606 for receiving the lateral edges of second blade 242. This configuration may help maximize available bone graft volume within the implant since the lateral edges of the blades serve as tracks for translation. Specifically, this limits the need for additional track members on the blade that would take up additional volume in the implant. Furthermore, the arrangement of the retaining channels and the associated blade edges results in most of the volume of the retaining channels being filled by the blade edges in the retracted position, which helps prevent any graft material or BGPM from entering the retaining channels and inhibiting normal blade travel.

Figure 13:
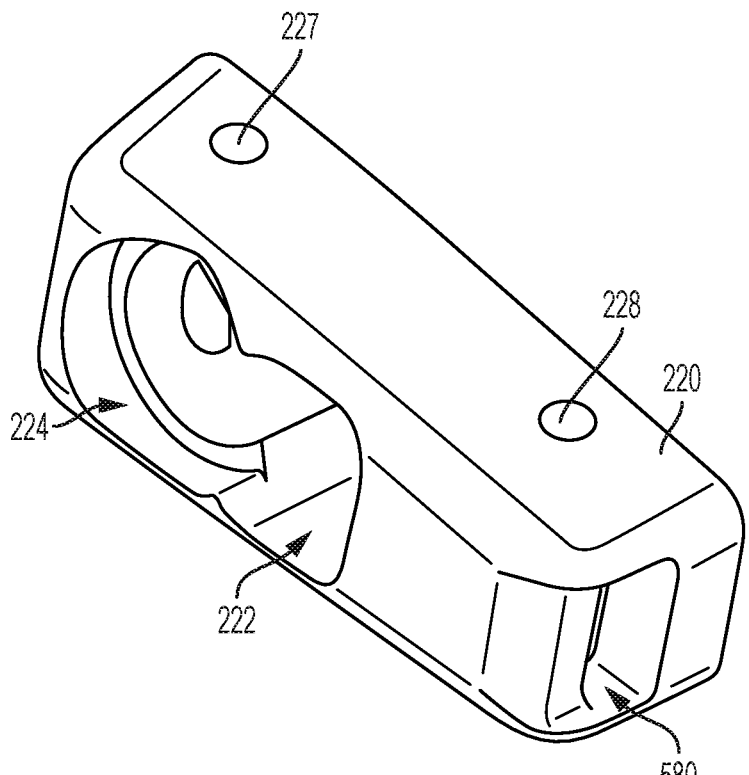
FIG. 13 is a schematic isometric view of a distal side of a cap of an implant, according to an embodiment.
Figure 14:
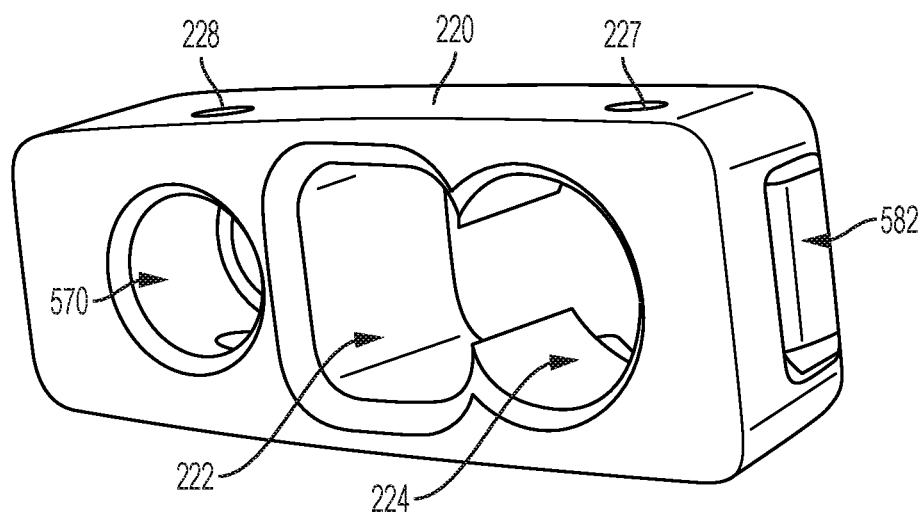
FIG. 14 is a schematic isometric view of a proximal side of the cap of FIG. 13.

FIGS. 13 and 14 illustrate isometric views of a distal side and a proximal side, respectively, of cap 220. Referring to FIGS. 13-14, cap 220 includes one or more openings for engaging different parts of implant 100. For example, cap 220 may include a first pin hole 227 and a second pin hole 228 that are configured to receive pin 291 and pin 292, respectively (see FIG. 3). Moreover, first pin hole 227 and second pin hole 228 (shown in FIGS. 13 and 14) of cap 220 may be aligned with corresponding holes in the body.

As previously discussed, cap 220 may include an opening 224 to receive a locking screw or other fastener. Additionally, cap 220 may include guide opening 222 that receives a portion of blade actuating member 260. In some embodiments, guide opening 222 may have a shape that matches the cross-sectional shape of a driven portion of a blade actuating member. In some embodiments, both guide opening 222 and driven shaft portion 320 of blade actuating member 260 have rectangular cross-sectional shapes. This configuration may allow axial motion, but control rotational and angular loads that could result during blade impaction as exemplified in FIGS. 13-14.

In some embodiments, cap 220 may include attachment points for an insertion instrument. For example, as seen in FIGS. 13-14, cap 220 may include a first cavity 580 and a second cavity 582 that may receive the ends of an insertion tool to improve the grip of the tool on implant 100 during insertion into (or removal from) between the vertebrae of the spine.

As seen in FIG. 14, in some embodiments, cap 220 may also include a cavity 570 for receiving a part of body 200. Specifically, cavity 570 may receive a fastening end 576 of body 200 (see FIG. 12), which includes a pin receiving opening 578 shown in FIG. 12, so that fastening end 576 can be retained within cavity 570 once second pin 292 has been inserted in the assembled and un-deployed state shown in FIG. 2.

Three Point Attachment

Figure 16:
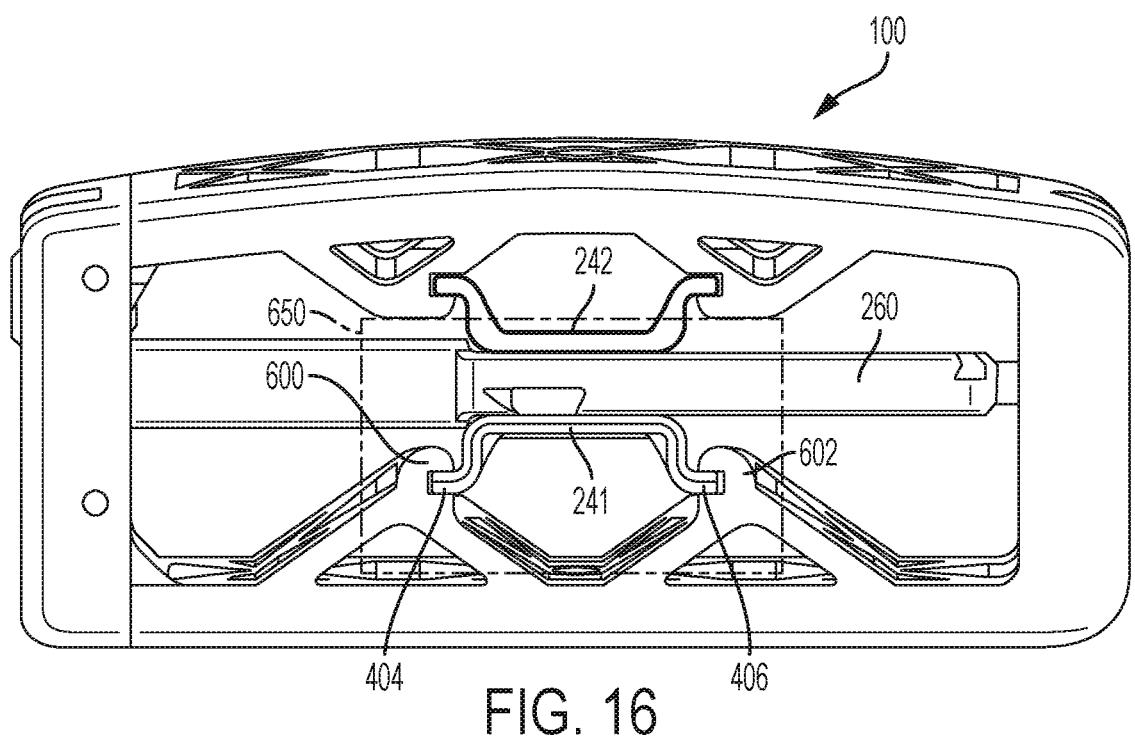
FIG. 16 is a top-down schematic view of an embodiment of an implant.
Figure 17:
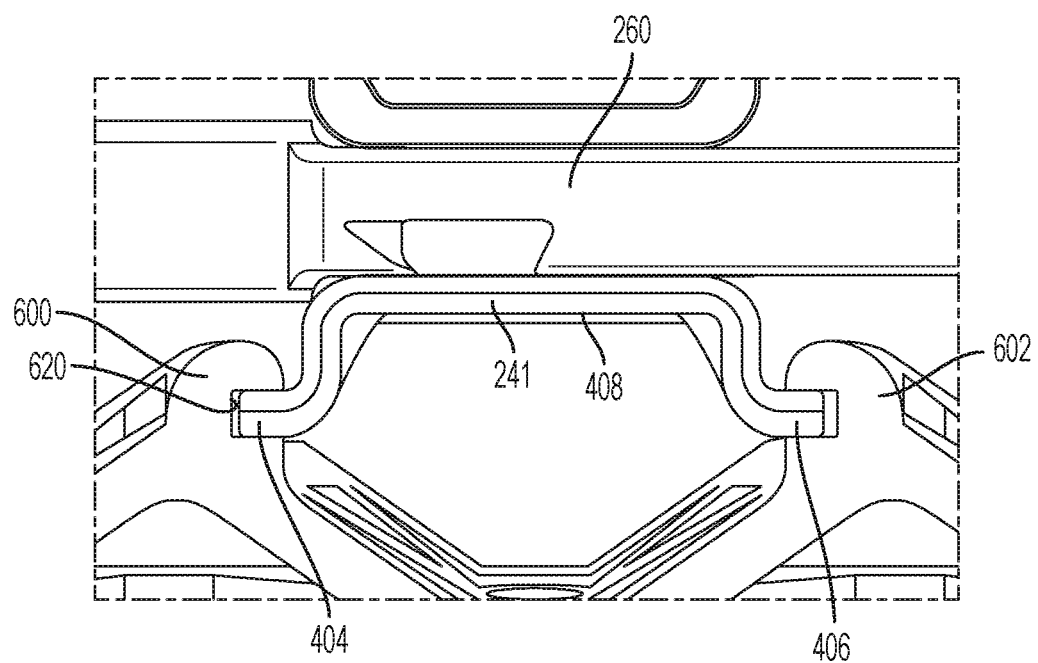
FIG. 17 is a top-down schematic view of a region of the implant of FIG. 16.

FIG. 16 is a schematic top view of implant 100 in which attachments between the blades and other components of implant 100 are visible. FIG. 17 is a schematic enlarged view of a region 650 of implant 100 including first blade 241 and a portion of blade actuating member 260, in which several attachment points are clearly visible.

Referring to FIGS. 16-17, implant 100 uses a three-point attachment configuration for each of first blade 241 and second blade 242. Specifically, each blade is received along its lateral edges by two blade retaining portions, and also coupled to blade actuating member 260 using the dovetail connection described above. As seen in FIG. 16, first lateral edge 404 of first blade 241 is received within the first blade retaining channel of first blade retaining portion 600. Second lateral edge 406 of first blade 241 is received within a second retaining channel of second blade retaining portion 602. Moreover, distal face 408 of first blade 241 remains unattached to any other elements of implant 100. Not only does first blade 241 remain unattached along distal face 408, but the entirety of distal face 408 between first lateral edge 404 and second lateral edge 406 is spaced apart from (i.e., not in contact with) all other elements of implant 100. Further, second blade 242 is likewise attached at its lateral edges to corresponding blade retaining portions and also coupled to blade actuating member 260 using a sliding dovetail connection. Thus, first blade 241 and second blade 242 are held in implant 100 using a three-point attachment configuration that may limit unwanted friction on first blade 241 and second blade 242 during impaction. It may be appreciated that the fit between each blade and each blade retaining channel may provide sufficient clearance to allow for translation of the blades along the retaining channels. In other words, the fit may not be so tight as to impede movement of the lateral edges within the retaining channels.

In different embodiments, the cross-sectional geometry of channels in one or more blade retaining portions could vary. In some embodiments, the cross-sectional geometry could be rounded. In the embodiment shown in FIG. 17, blade retaining portion 600 is seen to have a rectangular blade retaining channel 620. This rectangular geometry for the blade tracks or channels and tolerance allows for precise axial travel without binding from actuation ramp angular variations. Similarly, the remaining blade retaining portions of the embodiment of FIGS. 16-17 have similar rectangular shapes.

In some embodiments, the lateral edges of each blade may remain in the tracks or channels of each blade retaining portion while the blades are retracted to prevent bone graft material from restricting free deployment of the blades.

Sliding Connection

Using an interlocking joint, such as a dovetail sliding joint, to connect the blades and a blade actuating member helps prevent the blades from decoupling from the blade actuating member during impact. Additionally, with an interlocking joint the blade actuating member can be used to retract the blades.

Figure 19:
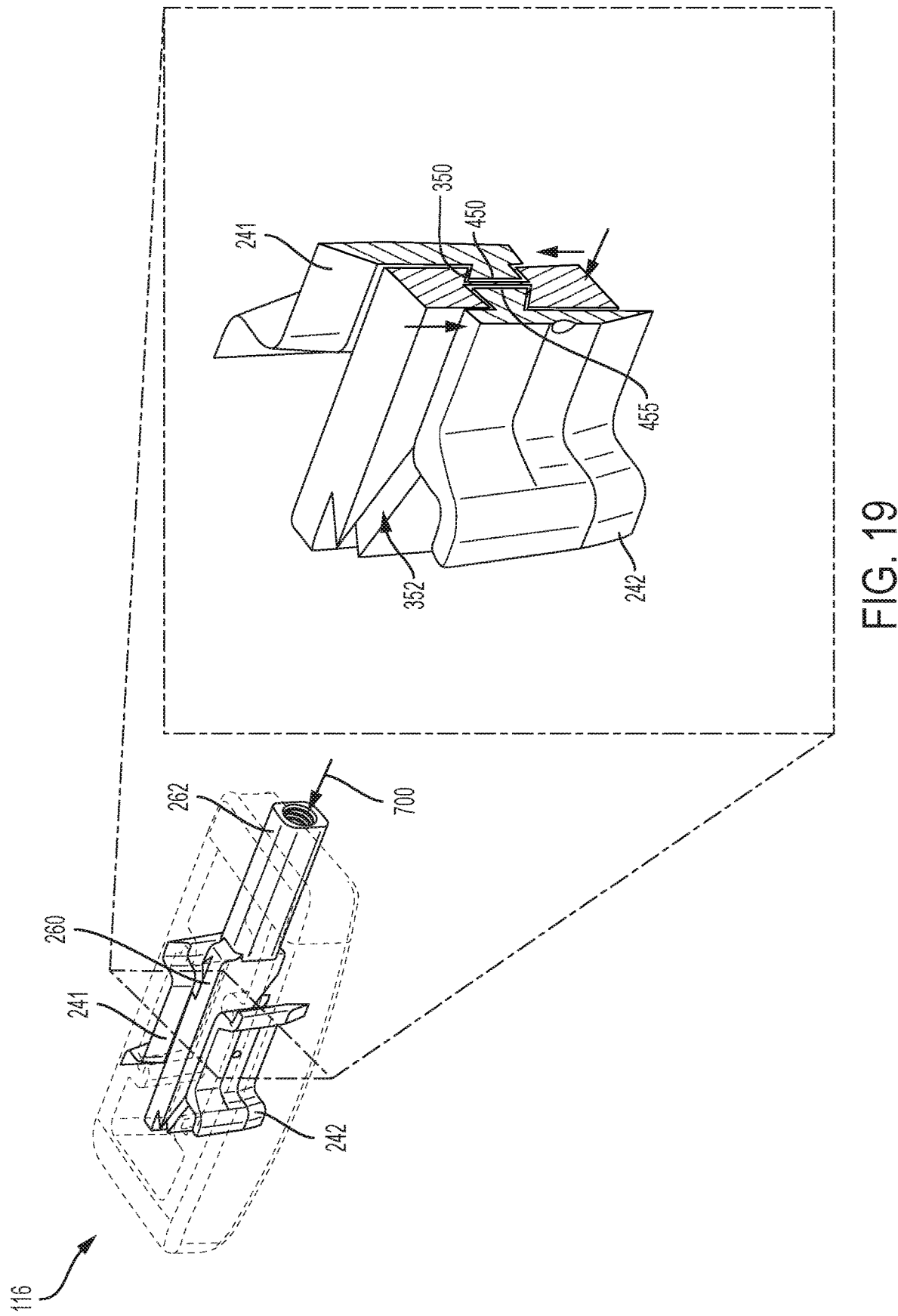
FIG. 19 is a schematic isometric view of the implant of FIG. 18 in an intermediate position, including an enlarged cut away view of the several components.
Figure 20:
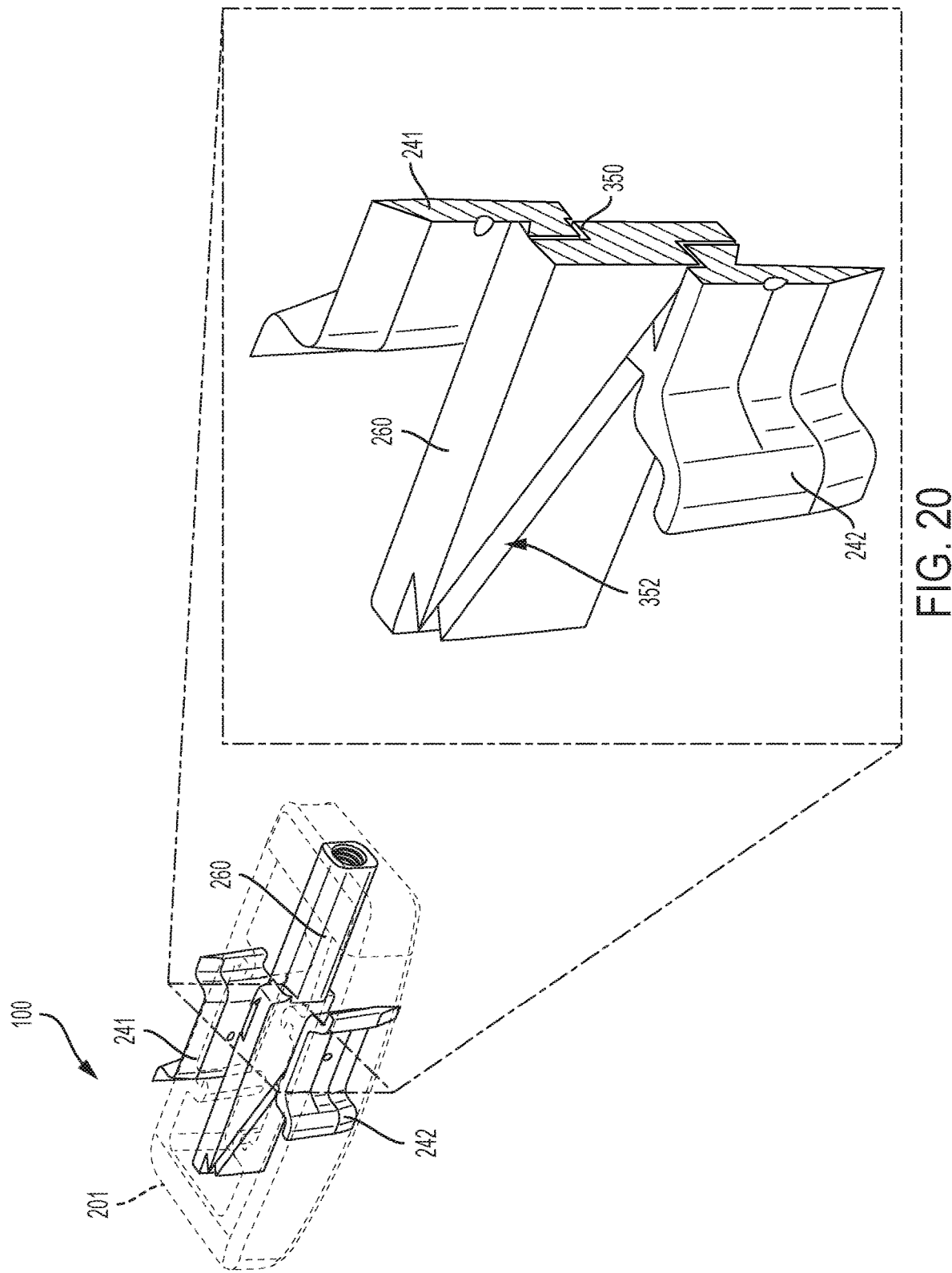
FIG. 20 is a schematic isometric view of the implant of FIG. 18 in a deployed position, including an enlarged cut away view of the several components.
Figure 21:
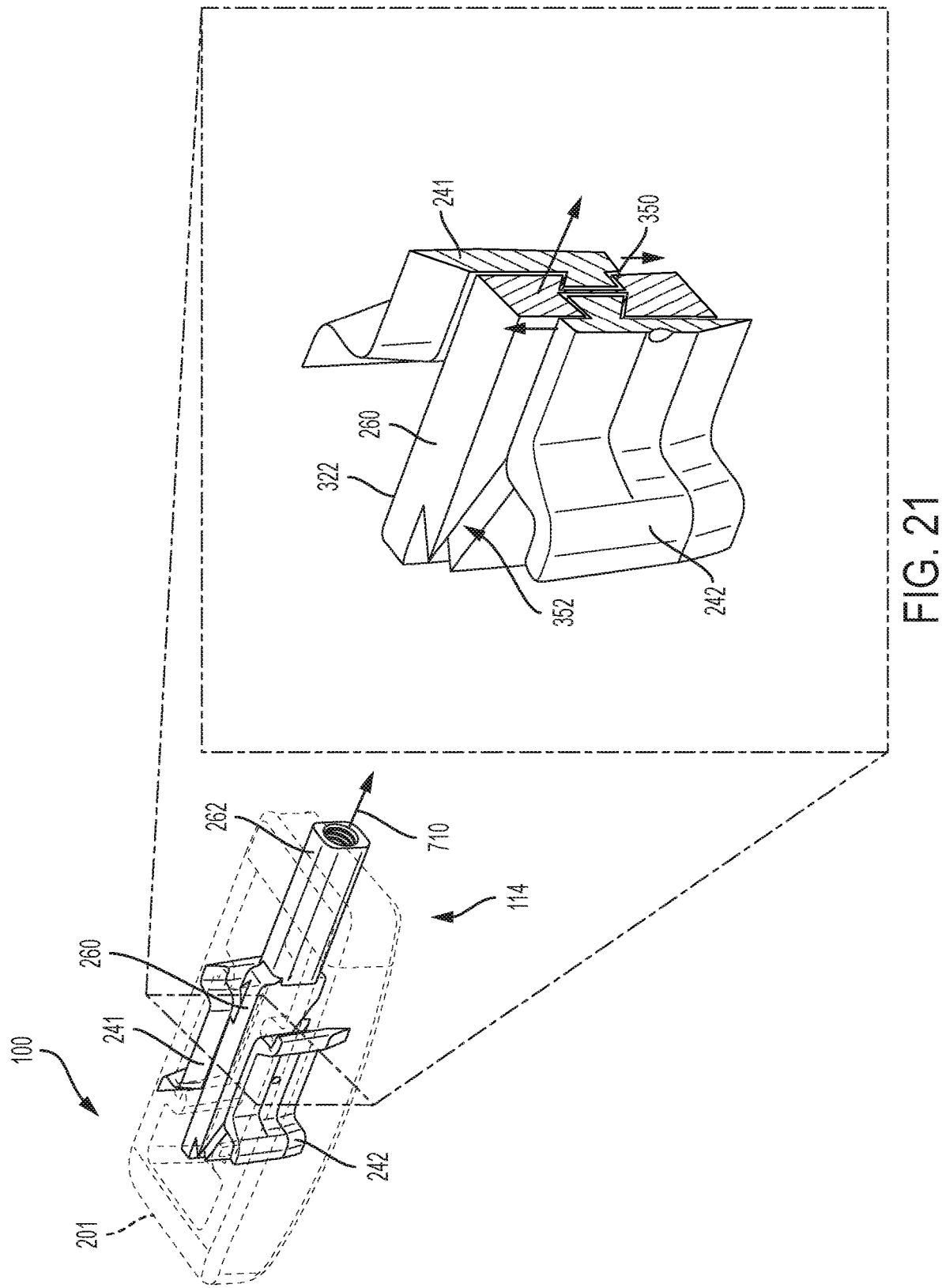
FIG. 21 is a schematic isometric view of the implant of FIG. 18 in an intermediate position, including an enlarged cut away view of the several components.

FIGS. 18-21 illustrate several schematic views of implant 100 during an impact sequence (FIGS. 18-20) as well as during a step of retracting the blades (FIG. 21). In FIGS. 18-21, outer structure 201 of implant 100 is shown in phantom to better show blade actuating member 260, first blade 241 and second blade 242. Also, each of FIGS. 18-21 include an enlarged cut-away view of a section of blade actuating member 260, first blade 241 and second blade 242 to better illustrate the coupling between these parts during actuation.

Figure 18:
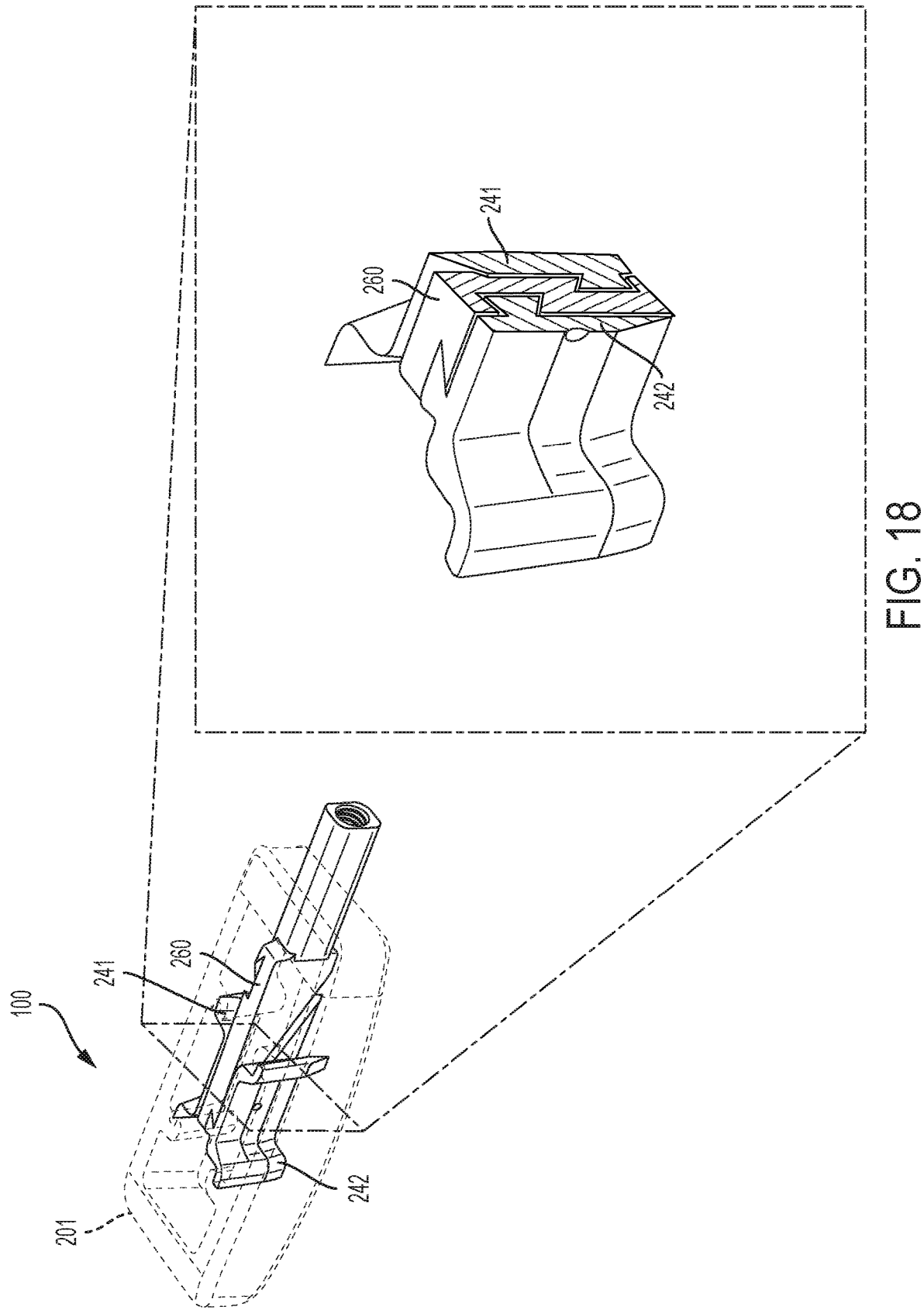
FIG. 18 is a schematic isometric view of an implant in an insertion position, including an enlarged cut-away view of several components, according to an embodiment.

In FIG. 18, implant 100 is in the insertion position, with first blade 241 and second blade 242 fully retracted within outer structure 201. Next, as seen in FIG. 19, an impacting force 700 is applied to driven end 262 of blade actuating member 260. As blade actuating member 260 is translated towards second lateral side 116 of implant 100, blade actuating member 260 applies forces to first blade 241 and second blade 242 along first channel 350 and second channel 352, respectively. Specifically, the orientation of first channel 350 is such that first blade 241 is forced towards the superior side of implant 100. Likewise, the orientation of second channel 352 is such that second blade 242 is forced towards the inferior side of implant 100. Furthermore, the interlocking connection between first protruding portion 450 and first channel 350 (as well as between second protruding portion 455 and second channel 352) means that both blades remain coupled to the motion of blade actuating member 260 at all times. It should be noted that since both blades are restricted from moving in a longitudinal direction (i.e., the direction of motion of blade actuating member 260), the resulting motion of each blade is purely vertical. Moreover, using the dovetail shaped protruding portions for each blade means the protruding portions are both lifting at the center line to limit any cocking force or rotational moments that could result in increased (friction) resistance to motion or binding of these moving parts.

Using this configuration, the forces deploying the blades are balanced through the blade actuating member 260 in order to minimize friction and binding between driven shaft portion 320 and opening 222 in cap 220 (see FIG. 3), which helps to guide blade actuating member 260 and keep its motion restricted to directions parallel to the longitudinal axis (see FIG. 2).

In FIG. 20, implant 100 has been placed in the fully deployed position, with both first blade 241 and second blade 242 fully extended from implant 100. As seen in the enlarged cut-away view, both first blade 241 and second blade 242 remain coupled with blade actuating member 260 when implant 100 is in the fully deployed position. Because of this coupling, the motion of blade actuating member 260 can be reversed to retract first blade 241 and second blade 242, as shown in FIG. 21.

Referring to FIG. 21, driven end 262 of blade actuating member 260 may be pulled in an opposing direction to the motion shown in FIG. 19. For example, in some embodiments a delivery tool can be coupled to driven end 262 using a threaded connector. Then, as the tip of the delivery tool is retracted a retracting or pulling force 710 may be applied to drive end 262. As blade actuating member 260 (and specifically, blade engaging portion 322) is pulled towards first lateral side 114 of implant 100, blade actuating member 260 applies forces to first blade 241 and second blade 242 along first channel 350 and second channel 352, respectively. Specifically, the orientation of first channel 350 is such that first blade 241 is forced towards the inferior side of implant 100. Likewise, the orientation of second channel 352 is such that second blade 242 is forced towards the superior side of implant 100. Although not shown, applying sufficient force at driven end 262 may result in full retraction of first blade 241 and second blade 242 so that implant 100 is returned to the insertion position shown in FIG. 18.

Locking Screw

Figure 22:
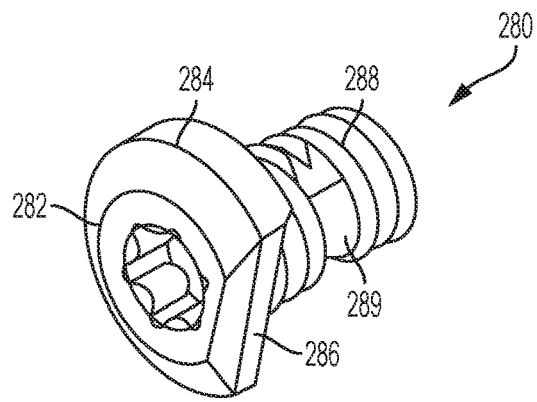
FIG. 22 is a schematic isometric view of a locking screw according to an embodiment.
Figure 23:
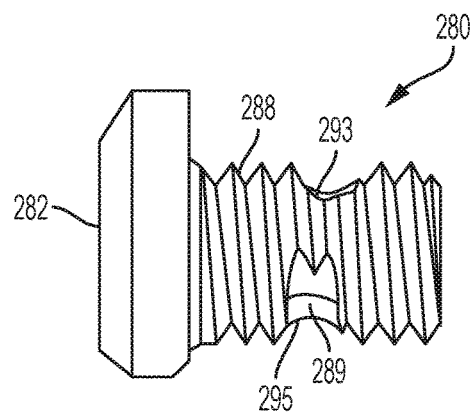
FIG. 23 is a schematic side view of the locking screw of FIG. 22.
Figure 24:
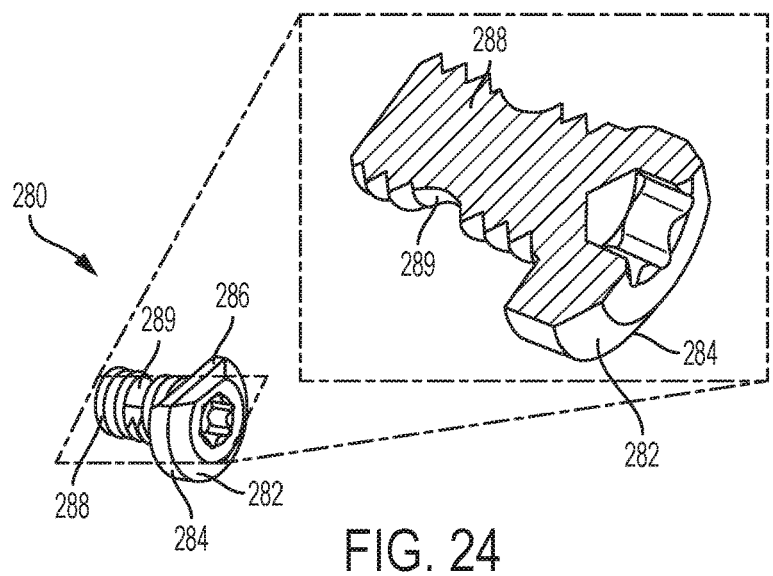
FIG. 24 is an isometric view of the locking screw of FIG. 22, including an enlarged cut-away view of the locking screw.

FIGS. 22-24 illustrate several schematic views of locking screw 280, according to an embodiment. Locking screw 280 includes a flanged head 282 with a rounded segment 284 and a flat segment 286. Locking screw 280 further includes a threaded body 288 and a rotation restricting groove 289.

Rotation restricting groove 289 may include a first groove end 293 and a second groove end 295 (see FIG. 23). As seen in FIGS. 22-24, rotation restricting groove 289 may extend less than a full turn around the circumference of threaded body 288.

Figure 25:
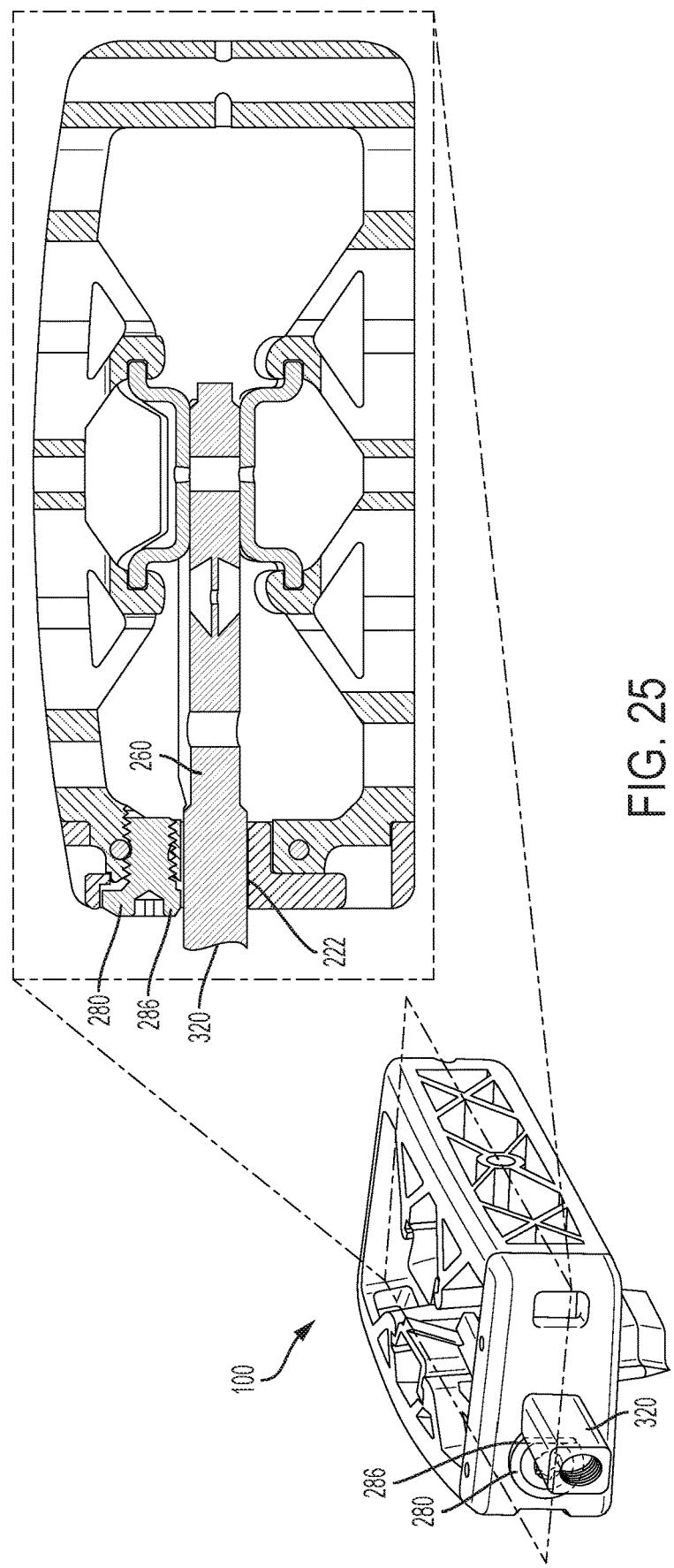
FIG. 25 is a schematic isometric view of an implant with a locking screw in a rotational position that allows a blade actuating member to extend from an implant, according to an embodiment.
Figure 26:
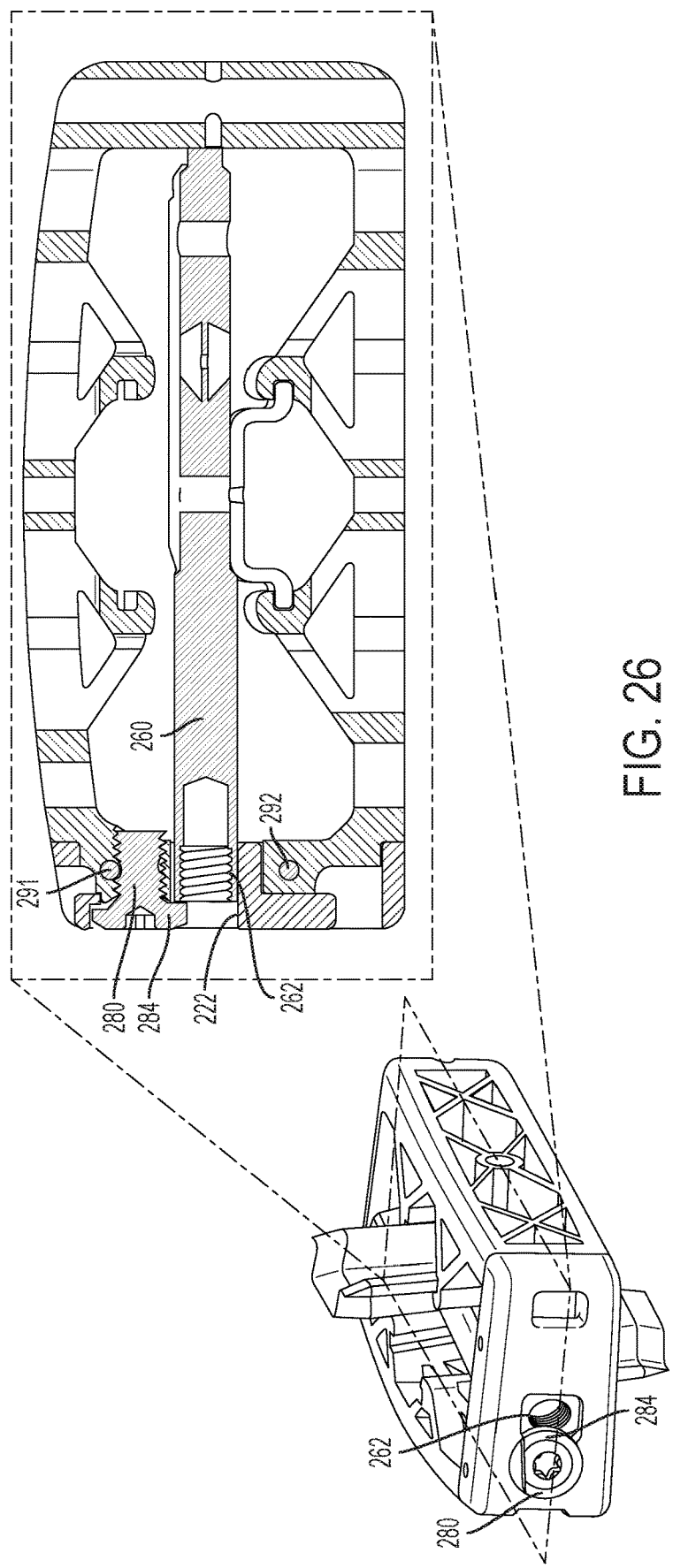
FIG. 26 is a schematic isometric view of the implant of FIG. 25 in which the locking screw has been rotated to prevent the blade actuating member from extending from the body of the implant.

FIGS. 25-26 illustrate schematic views of an implant, including an isometric view and an enlarged cross-sectional view taken near a transverse plane of implant 100. FIG. 25 is a schematic view of implant 100 with locking screw 280 in an "unlocked" rotational position. In this unlocked rotational position, locking screw 280 is rotated so that flat segment 286 is aligned with an adjacent edge of opening 222, thereby allowing driven shaft portion 320 of blade actuating member 260 to pass through opening 222 without impedance.

FIG. 26 is a schematic view of implant 100 with locking screw 280 in a "locked" rotational position. In this locked rotational position, locking screw 280 is rotated so that rounded segment 284 extends over opening 222 and blocks the passage of driven end 262 of blade actuating member 260 through opening 222. It may be appreciated that locking screw 280 can only be placed in the locked rotational position once driven end 262 has been pushed completely through opening 222 and is located proximally to locking screw 280.

As seen in FIG. 26, pin 291 may be disposed within rotation restricting groove 289 (see FIGS. 22-24) of locking screw 280. Moreover, rotation restricting groove 289 may be sized and dimensioned to allow locking screw to be rotated between the locked and unlocked positions, but not rotated to the point of completely backing out of implant 100. For example, with pin 291 engaged in rotation restricting groove 289, locking screw 280 may only be rotated between a first rotational position where pin 291 is disposed against first groove end 293 and a second rotational position where pin 291 is disposed against second groove end 295.

It may be appreciated that in some embodiments a blade actuating member (e.g., blade actuating member 260) may function to support adjacent vertebral bodies. This is can be accomplished by using a blade actuating member with a height similar to the height of the outer support structure so that the superior and inferior surfaces of the blade actuating member may come into contact with the vertebral bodies following implantation. Since the blade actuating member functions as a load bearing structure within the implant, this may free up additional space in the implant otherwise occupied by additional support structures, thereby increasing the internal volume available for bone graft or BGPMs.

Implant Dimensions

In different embodiments, the size of an implant could vary. In some embodiments, an implant could have any length. Embodiments could have lengths ranging from 40 mm to 60 mm. In some cases, a manufacturer could provide multiple implant options with lengths varying between 40 mm and 60 mm in 5 mm increments. In some embodiments, an implant could have any height. Embodiments could have a height ranging from 8 mm to 16 mm. In some cases, a manufacturer could provide implants with heights varying from 8 mm to 16 mm in 2 mm increments. Embodiments could have widths (i.e., size along the posterior-anterior axis) of 18 mm, 22 mm, 26 mm as well as other sizes.

Embodiments can also be constructed with various lordosis angles, that is, angles of incline between the posterior and anterior sides. Embodiments could be configured with lordosis angles of 8, 15 and 20 degrees, for example. In other embodiments, other lordosis angles could be used for an implant.

Alignment Features

Embodiments may optionally include one or more alignment features. Exemplary alignment features include, but are not limited to, windows for fluoroscopy positioning, windows for blade deployment validation, windows for aligning a blade actuating member with one or more blades, as well as various other kinds of alignment features. Referring to FIG. 2, body 200 of implant 100 includes a central alignment window 209. Additionally, blade 241 includes an alignment window 297. Alignment window 297 may align with central alignment window 209 when blade 241 is fully retracted. Moreover, blade actuating member 260 includes a first alignment window 277 and a second alignment window 279. Window 277 and window 279 may align with the implant body center line when blade 241 and blade 242 are fully deployed and retracted. One or more of these windows (i.e., central alignment window 209, first alignment window 277 and/or second alignment window 279) may facilitate fluoroscopy positioning and may be used to confirm blade deployment. For example, in some cases, when first blade 241 and second blade 242 are fully deployed, the blades may clear first alignment window 277 of blade actuating member 260.

Some embodiments may also include one or more stroke limiting stops. For example, the embodiment of implant 100 shown in FIG. 2 includes a first stroke limiting stop 283 and second stroke limiting stop 287 on blade actuating member 260. These stops may help prevent over travel of blade actuating member 260. Specifically, stop 283 and stop 287 may contact the internal surfaces of body 200.

Materials

The various components of an implant may be fabricated from biocompatible materials suitable for implantation in a human body, including but not limited to, metals (e.g. titanium, titanium alloy, stainless steel, cobalt-chrome, or other metals), synthetic polymers (e.g. PEEK or PEKK), ceramics, and/or their combinations, depending on the particular application and/or preference of a medical practitioner.

Generally, the implant can be formed from any suitable biocompatible, non-degradable material with sufficient strength. Typical materials include, but are not limited to, titanium, biocompatible titanium alloys (e.g. Titanium Aluminides (including gamma Titanium Aluminides), $Ti_6$—$Al_4$—V ELI (ASTM F 136 and ASTM F 3001), or $Ti_6$—$Al_4$—V (ASTM F 1108, ASTM F 1472, and ASTM F 2989) and inert, biocompatible polymers, such as polyether ether ketone (PEEK) (e.g. PEEK-OPTIMA®, Invibio Inc, Zeniva®, Solvay Inc., or others). Optionally, the implant contains a radiopaque marker to facilitate visualization during imaging when constructed of radiolucent biomaterials.

In different embodiments, processes for making an implant can vary. In some embodiments, the entire implant may be manufactured and assembled via traditional and CNC machining, injection-molding, cast or injection molding, insert-molding, co-extrusion, pultrusion, transfer molding, overmolding, compression molding, 3-Dimensional (3-D) printing, dip-coating, spray-coating, powder-coating, porous-coating, milling from a solid stock material and their combinations.

In one embodiment, body 200 may be produced by Direct Metal Laser Sintering (DMLS) using powder Ti-6Al-4V ELI, and then traditional or CNC machined in specific locations to precise dimensions. Moreover, in one embodiment, blade actuating member 260, first blade 241, second blade 242, cap 220, pins 290 and locking screw 280 may also be made of a material including titanium.

Implantation

Some embodiments may use a bone growth promoting material, including bone graft or bone graft substitute material. As used herein, a "bone growth promoting material" (BGPM) is any material that helps bone growth. Bone growth promoting materials may include provisions that are freeze dried onto a surface or adhered to the metal through the use of linker molecules or a binder. Examples of bone growth promoting materials are any materials including bone morphogenetic proteins (BMPs), such as BMP-1, BMP-2, BMP-4, BMP-6, and BMP-7. These are hormones that convert stem cells into bone forming cells. Further examples include recombinant human BMPs (rhBMPs), such as rhBMP-2, rhBMP-4, and rhBMP-7. Still further examples include platelet derived growth factor (PDGF), fibroblast growth factor (FGF), collagen, BMP mimetic peptides, as well as RGD peptides. Generally, combinations of these chemicals may also be used. These chemicals can be applied using a sponge, matrix or gel.

Some bone growth promoting materials may also be applied to an implantable prosthesis through the use of a plasma spray or electrochemical techniques. Examples of these materials include, but are not limited to, hydroxyapatite, beta tri-calcium phosphate, calcium sulfate, calcium carbonate, as well as other chemicals.

A bone growth promoting material can include, or may be used in combination with a bone graft or a bone graft substitute. A variety of materials may serve as bone grafts or bone graft substitutes, including autografts (harvested from the iliac crest of the patient's body), allografts, demineralized bone matrix, and various synthetic materials.

Some embodiments may use autograft. Autograft provides the spinal fusion with calcium collagen scaffolding for the new bone to grow on (osteoconduction). Additionally, autograft contains bone-growing cells, mesenchymal stem cells and osteoblast that regenerate bone. Lastly, autograft contains bone-growing proteins, including bone morphogenic proteins (BMPs), to foster new bone growth in the patient.

Bone graft substitutes may comprise synthetic materials including calcium phosphates or hydroxyapatites, stem cell containing products which combine stem cells with one of the other classes of bone graft substitutes, and growth factor containing matrices such as INFUSE® (rhBMP-2-containing bone graft) from Medtronic, Inc.

It should be understood that the provisions listed here are not meant to be an exhaustive list of possible bone growth promoting materials, bone grafts or bone graft substitutes.

In some embodiments, BGPM may be applied to one or more outer surfaces of an implant. In other embodiments, BGPM may be applied to internal volumes within an implant. In still other embodiments, BGPM may be applied to both external surfaces and internally within an implant.

While various embodiments have been described, the description is intended to be exemplary, rather than limiting, and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with, or substituted for, any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

What is claimed is:

1. An implant, comprising:
   a body having a superior surface and an inferior surface, a superior-inferior axis extending through the superior surface and the inferior surface, and a lateral axis extending laterally through the body in a direction substantially perpendicular to the superior-inferior axis;
   a first blade having a first retracted position in the body and a first extended position where the first blade extends outwardly from the body;
   a blade actuating member configured to translate through the body in directions parallel to the lateral axis;
   wherein, when the blade actuating member is moved in a first direction along the lateral axis, the first blade moves towards the first extended position;
   wherein, the motion of the blade actuating member can be reversed, such that, when the blade actuating member is moved in a second direction opposite the first direction, the first blade moves towards the first retracted position;
   wherein, in the first extended position, the first blade extends from the superior surface at a first non-zero angle with respect to the superior-inferior axis.

2. The implant according to claim 1, further including a second blade having a second retracted position in the body and a second extended position where the second blade extends outwardly from the body;
   wherein, when the blade actuating member is moved in the first direction along the lateral, the second blade moves towards the first extended position;
   wherein when the blade actuating member is moved in the second direction opposite the first direction, the second blade moves towards the second retracted position;
   wherein, in the second extended position, the second blade extends from the inferior surface at a second non-zero angle with respect to the superior-inferior axis.

3. The implant according to claim 1, wherein the first blade extends from a first location offset from a centerline of the body; and
   wherein the first blade is angled toward the centerline of the body.

4. The implant according to claim 3, wherein the second blade extends from a second location offset from the centerline of the body and opposite the first location; and
   wherein the second blade is angled toward the centerline of the body, such that the first non-zero angle and the second non-zero angle are substantially equal and opposite one another.

5. The implant according to claim 1, wherein the first blade has an outer edge, an inner edge, a first lateral edge and a second lateral edge, and wherein the first blade is only in contact with the body along the first lateral edge and the second lateral edge.

6. The implant according to claim 5, wherein the body includes a first retaining channel to hold the first lateral edge and wherein the body includes a second retaining channel to hold the second lateral edge, and wherein the first retaining channel and the second retaining channel are each oriented at a non-zero angle with respect to the first lateral axis.

7. An implant, comprising:
   a body having a superior surface, an inferior surface, an anterior surface, and a posterior surface, a superior-inferior axis extending through the superior surface and the inferior surface, a lateral axis extending laterally through the body in a direction substantially perpendicular to the superior-inferior axis, and an anterior-posterior axis extending through the anterior surface and the posterior surface and in a direction that is substantially perpendicular to the superior-inferior axis and substantially perpendicular to the lateral axis;
   a first deployable blade having a first retracted position in the body and a first extended position where the first blade extends outwardly from the body, the blade having a longitudinal axis extending in a direction of blade deployment;
   a blade actuating member that can translate through the body in directions parallel to the lateral axis;
   wherein, when the blade actuating member is moved in a first direction along the lateral axis, the first blade moves in a superior direction towards the first extended position;
   wherein, when the blade actuating member is moved in a second direction opposite the first direction, the first blade moves in an inferior direction towards the first retracted position;
   the first blade having a channel-like geometry forming a substantially C-shaped cross-sectional shape in a plane perpendicular to the longitudinal axis of the first blade, the C-shaped cross-sectional shape being defined by a first portion extending in a direction substantially parallel with the lateral axis, a second portion extending from a first end of the first portion at a non-zero angle toward the posterior surface of the body, and a third portion extending from a second end of the first portion at a non-zero angle toward the posterior surface of the body.

8. The implant according to claim 7, further including a second blade having a second retracted position in the body and a second extended position where the second blade extends outwardly from the body;

wherein, when the blade actuating member is moved in the first direction along the lateral axis, the second blade moves in an inferior direction towards the second extended position;

wherein, when the blade actuating member is moved in the second direction opposite the first direction, the second blade moves in a superior direction towards the second retracted position;

the second blade having a channel-like geometry forming a substantially C-shaped cross-sectional shape defined by a first portion extending in a direction substantially parallel with the lateral axis, a second portion extending from a first end of the first portion at a non-zero angle toward the posterior surface of the body, and a third portion extending from a second end of the first portion at a non-zero angle toward the anterior surface of the body.

9. The implant according to claim 8, wherein the first blade extends from a first location offset from a centerline of the body; and wherein the first blade is angled toward the centerline of the body.

10. The implant according to claim 9, wherein the second blade extends from a second location offset from the centerline of the body and opposite the first location; and wherein the second blade is angled toward the centerline of the body, such that the first non-zero angle and the second non-zero angle are substantially equal and opposite one another.

11. The implant according to claim 7, wherein the blade actuating member is coupled to the first blade by a sliding joint.

12. The implant according to claim 11, wherein the blade actuating member includes a channel and wherein the first blade includes a protruding portion that fits within the channel.

13. The implant according to claim 12, wherein the channel in the blade actuating member and the protruding portion together form a sliding dovetail joint.

14. An implant, comprising:
an outer structure, the outer structure having a first axis;
a blade, the blade having a retracted position in the outer structure and an extended position where the blade extends outwardly from the outer structure;
a blade actuating member configured to translate through the outer structure in directions parallel to the first axis;
wherein the blade actuating member is coupled to the blade and can move the blade in a first direction from the retracted position to the extended position; and
wherein the motion of the blade actuating member can be reversed, such that, when the blade actuating member is moved in a second direction opposite the first direction, the blade moves towards the retracted position; and
an anti-retraction system incorporated into the outer structure and configured to prevent the blade actuating member from backing out of the outer structure of the implant.

15. The implant according to claim 14, wherein the anti-retraction system further includes a locking screw configured to be rotated between an unlocked rotational position in which a driven end of the blade actuating member can pass through a guide opening in the outer structure and a locked rotational position, in which the driven end of the blade actuating member is prevented from moving through the guide opening.

16. The implant according to claim 15, wherein the locking screw includes a threaded portion and a flange portion, wherein the flange portion includes a rounded segment and a flat segment.

17. The implant according to claim 16, wherein the flat segment is aligned with an edge of the guide opening in the unlocked rotational position and wherein the rounded segment is disposed over the edge of the guide opening in the locked rotational position.

18. The implant according to claim 16, wherein the outer structure further includes a body and a cap; and wherein the anti-retraction system further includes a pin that extends through the body and the cap and helps secure the body to the cap.

19. The implant of claim 18, wherein the threaded portion of the locking screw includes a rotation constraining groove;

wherein the rotation constraining groove includes a first groove end and a second groove end;

wherein the rotation constraining groove extends less than one full rotation around the circumference of the threaded portion; and wherein the pin extends partially through the body and engages the rotation constraining groove.

20. The implant according to claim 19, wherein the locking screw is constrained to rotate between a first rotational position and a second rotational position, the first rotational position being a position where the pin is disposed adjacent the first groove end and the second rotational position being a position where the pin is disposed adjacent the second groove end.

* * * * *